(12) United States Patent
Garegnani et al.

(10) Patent No.: US 11,478,503 B2
(45) Date of Patent: Oct. 25, 2022

(54) VITAMIN B12 COMPOUND SUPPLEMENTATION METHODS AND COMPOSITIONS

(71) Applicant: LUPIN, INC., Baltimore, MD (US)

(72) Inventors: James A Garegnani, Hopewell, NJ (US); Richard Holl, Rolla, MO (US); Gregory Kaufman, Short Hills, NJ (US)

(73) Assignee: Lupin, Inc., Baltimore, MD (US)

( * ) Notice: Subject to any disclaimer, the term of this patent is extended or adjusted under 35 U.S.C. 154(b) by 0 days.

(21) Appl. No.: 16/951,994

(22) Filed: Nov. 18, 2020

(65) Prior Publication Data

US 2021/0154223 A1    May 27, 2021

Related U.S. Application Data

(60) Provisional application No. 62/938,724, filed on Nov. 21, 2019.

(51) Int. Cl.

| *A61K 31/714* | (2006.01) |
|---|---|
| *A61K 9/20* | (2006.01) |
| *A23L 33/15* | (2016.01) |
| *A61K 31/57* | (2006.01) |
| *A61K 31/566* | (2006.01) |

(52) U.S. Cl.
CPC ............ *A61K 31/714* (2013.01); *A23L 33/15* (2016.08); *A61K 9/2013* (2013.01); *A61K 31/566* (2013.01); *A61K 31/57* (2013.01)

(58) Field of Classification Search
CPC .. A61K 31/714; A61K 9/2013; A61K 31/566; A61K 31/57; A23L 33/15
USPC ......................................................... 514/52
See application file for complete search history.

(56) References Cited

U.S. PATENT DOCUMENTS

| 4,530,839 | A |  | 7/1985 | Pasquale |  |
|---|---|---|---|---|---|
| 5,716,941 | A |  | 2/1998 | Rabinoff |  |
| 2003/0190381 | A1 |  | 10/2003 | Bland |  |
| 2004/0157783 | A1 |  | 8/2004 | McCaddon |  |
| 2007/0111975 | A1 | * | 5/2007 | Diliberti | A61P 15/18 |
|  |  |  |  |  | 514/170 |
| 2008/0038343 | A1 |  | 2/2008 | King |  |
| 2008/0038367 | A1 |  | 2/2008 | Saloum |  |
| 2013/0005679 | A1 |  | 1/2013 | Bhatia |  |

FOREIGN PATENT DOCUMENTS

WO      2007085888      8/2007

OTHER PUBLICATIONS

Moll et al. Iron, vitamin B12 and folate. Medicine 45:4, p. 198-203, 2017. (Year: 2017).*
Allen, et al., "Diagnosis of Cobalamin Deficiency I: Usefulness of Serum Methylmalonic Acid and Total Homocysteine Concentrations", American Journal of Hematology, vol. 34, Issue 2, Abstract, 1 page, Jun. 1990).
Lindenbaum, et al., "Neuropsychiatric Disorder Cause by Cobalamin Deficiency in the Absence of Anemia or Macrocytosis", The New England Journal of Medicine, 1988, 318:1720-1728.
Estarylla, Prescribing Information; Initial U.S. Approval 1989, (20 pages).
Lindenbaum, et al., "Diagnosis of Cobalamin Deficiency: II. Relative Sensitivities of Serum Cobalamin, Methylmalonic Acid, and Total Homocysteine Concentrations", American Journal of Hematology, vol. 34, Issue 2. Abstract, 1 page, Jun. 1990).
Moelby, et al., "The Relationship Between Clinically Confirmed Cobalamin Deficiency and Serum Methylmalonic Acid", Journal of Internal Medicine, vol. 228, Issue 4, 1 page, Oct. 1990).
Pennypacker, et al., "High Prevalence of Cobalamin Deficiency in Elderly Outpatients", Journal of American Geriatrics Society, vol. 40, Issue 12, (2 pages, Dec. 1992).
Tri-Previfem, Prescribing Information, Initial U.S. Approval 1989, (18 pages).
Tri-Sprintec product label, (29 pages, Sep. 2011).
Tri-Lo-Marzia, Prescribing Information, Initial U.S. Approval 1989, (19 pages).
TriNessa Tablets product label, (23 pages, May 2008).
Ueland, et al., "Plasma Homocysteine, A Risk Factor for Premature Vascular Disease. Plasma Levels in Healthy Persons; During Pathologic Conditions and Drug Therapy", Nord Med 1989; 104(11): 293-8.
International Search Report and Written Opinion for PCT/US20/61128 dated Feb. 11, 2021.
International Preliminary Report On Patentability for PCT/US2020/061128 dated Nov. 2, 2021.
Ortho Tri-Cyclen Product Label; Janssen Pharmaceuticals, Inc. Initial date of approval 1989. Revised Aug. 2008.

* cited by examiner

*Primary Examiner* — Yih-Horng Shiao
(74) *Attorney, Agent, or Firm* — Transformative Legal LLC; Len S. Smith; Denise M. Brown

(57) ABSTRACT

The invention described herein provides new methods and compositions for the cyclical provision of a vitamin B12 compound in a dosing regimen wherein the total amount of vitamin B12 administered during any one treatment cycle does not exceed 35 mcg. More specifically, the invention described in this disclosure promotes the prevention or treatment of a vitamin B12 deficiency, supports the replenishment and or maintenance of healthy blood cell levels, or both, particularly in those experiencing a periodic physiological challenge which may compromise vitamin B12 status or result in an increased requirement for vitamin B12, such as the monthly blood loss experienced by a reproductively cycling human female.

20 Claims, No Drawings

VITAMIN B12 COMPOUND SUPPLEMENTATION METHODS AND COMPOSITIONS

CROSS REFERENCE TO RELATED APPLICATIONS

This application claims priority to U.S. Provisional Patent Application No. 62/938,724, filed Nov. 21, 2019, titled, "Vitamin B12 Compound Supplementation Methods and Compositions," the entirety of which is incorporated by reference herein.

FIELD OF THE INVENTION

The invention described in this disclosure relates to new regimens for the administration of vitamin B12 compounds to mammalian subjects (e.g., human female patients) for the promotion or maintenance of health and to compositions that are configured to facilitate the practice of such new vitamin B12 compound administration methods.

BACKGROUND OF THE INVENTION

Vitamin B12 is an essential nutrient which research has demonstrated plays a role in DNA synthesis and regulation, fatty acid synthesis, physiological energy processes, and cellular metabolism. Commonly available vitamin B12 supplements provide the vitamin B12 nutrient/active ingredient in one of two forms: cyanocobalamin or methylcobalamin. Common dosages of Vitamin B12 in leading Vitamin B12 supplements provide daily doses of between about 50 mcg (micrograms) and about 10,000 mcg. These levels reflect numerous reported clinical studies for various conditions in which the amount of continuous daily vitamin B12 supplementation associated with positive health outcomes ranged from, e.g., 20 mcg to 1,000 mcg.

Based on such clinical studies and otherwise, supplementation with vitamin B12 has been alleged to be associated with the maintenance or enhancement of a broad range of physiological conditions and processes ranging from reducing depression and cognitive impairment to treating age-related macular degeneration. Perhaps correspondingly, vitamin B12 deficiencies also have been allegedly linked with a number of negative health conditions including fatigue, shortness of breath, skin conditions, gastrointestinal problems, vision problems, nerve problems, and even cognitive functioning issues such as memory loss. Subsets of the population have been identified as being particularly susceptible to vitamin B12 deficiency, including older individuals (e.g., individuals over 50 years of age). However, other recent studies have suggested that vitamin B12 supplementation can contribute to an increased risk of cancer. Thus, the safety and risk/benefit profile of supplementation with the currently leading vitamin B12 supplement regimens may be less clear than similar leading vitamin or mineral supplements.

SUMMARY OF THE INVENTION

The invention described herein provides new methods and compositions for promoting or maintaining health or preventing or treating conditions in mammalian subjects, such as humans, such as females, for example females experiencing a recurring vaginal discharge of blood, e.g. menstruating and potentially menstruating females or females experiencing or at risk for experiencing breakthrough bleeding while on a birth control method that regulates ovulation, such as a hormonal birth control regimen.

The methods of the invention comprise administering one or more vitamin B12 compounds to such a mammalian host, typically in significantly lower amounts on a daily and/or periodic basis (e.g., over a period of about one month) than is associated with current leading vitamin B12 supplementation regimens.

The methods of the invention can in some aspects be performed for the promotion or maintenance of health or the prevention or treatment of conditions, such as the prevention or treatment of a vitamin B12 deficiency, enhancement in blood cell level, or modulation of another nutritional or medical condition that is modulated by vitamin B12. In one aspect, the inventive methods comprise administering a vitamin B12 compound-containing dosage form promoting or facilitating promotion of one or more vitamin B12-effects, such as replenishment or maintenance of healthy blood cell levels in a mammal, such as in a female (e.g., a female that experiences menstruation or breakthrough bleeding).

The inventive vitamin B-12 compound supplementation methods of the invention typically can be characterized by comprising the administration of:

(a) relatively low doses of vitamin B12 compounds (as compared to current vitamin B12 supplementation regimens), based on
  (i) a per-dosage (and, typically, per day) basis (e.g., by administering less than 5 mcg a day, less than 4 mcg a day, or less than about 3 mcg of a vitamin B12 compound a day, such as about 2-5 mcg/day or 2-3 mcg/day),
  (ii) a per treatment period basis (e.g., by delivering a maximum of 50 mcg vitamin B12 compound/month, such as a maximum of about 40 mcg/month, about 35 mcg/month, or about 30 mcg/month, for example, about 15-45 mcg/month, about 17.5-37.5 mcg/month, about 20-35 mcg/month, or about 20-30 mcg/month), or
  (iii) based on a regimen that is in accordance with both (i) and (ii);
(b) administration of the vitamin B12 compound(s) by way of a non-continuous, typically cyclic, administration regimen over one or more defined periods of time (e.g., administration of the vitamin B12 compound(s) during only about 7 days of a period of about a month, such as a period of 4 weeks), or
(c) a regimen that is accordance with both (a) and (b) above.

In a non-continuous administration regimen, one or more vitamin B12 compounds is administered to a subject during a certain portion of a defined period (e.g., about one week of about one month) and no vitamin B12 compound is administered to the subject during other days of the period. Such treatment and non-treatment periods can, according to certain aspects of the invention, repeat at least 2, 3, 4, 6, 9, 12, 15, 18, 20, 24, 30, 48, 60 or even more times (e.g., about 2-12 times, about 2-25 times, about 2-50 times, about 2-120 times, about 2-240 times, about 2-360 times, or even about 2-about 500 times) in a "cycle" comprising treatment days and non-treatment days. Such regimens are variously described in this disclosure as "cyclic regimens" or by similar descriptors such as "cyclic" administration, dosing, supplementation, treatment, or regimen. In some respects, the terms non-continuous, cyclic, and intermittent are used to similarly describe such methods of the invention, although a non-continuous or intermittent regimen also can more broadly indicate any regimen in which the vitamin B12 compound is not administered continuously over a longer period, even if any periods of administration of vitamin B12 compound administration and non-administration in such a regimen do not repeat in a generally regular cycle (though such an intermittent regimen can comprise several separate periods of vitamin B12 compound administration).

In one aspect of the invention, the treatment period of a cycle (i.e., the period when the vitamin B12 compound is administered to the subject) in a cyclic regimen corresponds with or is expected to correspond with the occurrence or likely occurrence of a recurring or potentially recurring physiological event in the subject. In one aspect, the expected event is a recurring vaginal discharge of blood (e.g., due to menstruation or breakthrough bleeding).

Thus, according to particular embodiments, the vitamin B12 dosage form is not administered daily but instead is administered over the course of a defined time period, which typically is a limited portion of a larger period, which can repeat 2, 3, or more times as a cycle of active treatment and inactivity (with respect to administration of the vitamin B12 compound composition). According to certain embodiments, the vitamin B12 compound is administered over the course of a treatment period comprising or consisting of, for example, 1-15 consecutive treatment days, such as for example between about 3-10 consecutive days (e.g., 2-12 days, 4-9 days, 3-9 days, or 4-8 days, such as 7 days).

In some aspects, the vitamin B12 dosage form is administered to a human female experiencing a recurring vaginal discharge of blood, or an otherwise reproductively cycling human female over a treatment period expected to correspond to the woman's monthly reproductive hormone cycle. Such a monthly reproductive hormone cycle could be a naturally occurring menstruation cycle or a cycle controlled by a hormone treatment regimen. In some aspects, the 1-15 or other selected consecutive day treatment period (e.g., a 2-12 day period, 3-10 day period, 5-9 day period, or about 7 day period) is expected to correlate with the period of the cycle when a woman's hematopoietic system is challenged and/or blood levels reduced, such as the period of time in which a vaginal discharge of blood (e.g. menstruation or a breakthrough bleed) occurs causing a depletion in otherwise normal blood cell levels.

According to some aspects, the methods of the invention comprise not administering any vitamin B12 compound dosage form to the woman on any days other than the defined treatment days of a period or a cycle. In some embodiments, days other than defined treatment days (i.e., non-treatment days of the cycle) can range from about 16-about 30 consecutive days preceding or following a vitamin B12 compound treatment period (e.g., a period of about 15-27 days, such as about 18-25 days, e.g., about 19-23 days, or more particularly about 20-22 days, such as 21 days).

Together the treatment period (treatment days) and non-treatment period (or days) of a combined defined period of a cycle make up what can be considered the total period of the cycle (which may be called a cycle period or simply a cycle). Thus, e.g., a treatment period of about 7 days and a non-treatment period of about 21 days make up a total cycle period of about 28 days.

In certain embodiments, the invention provides a method for providing a vitamin B12 compound dosage form to a subject over the course of a restricted time period such as over the course of between about 1-about 15 consecutive days (e.g., about 4-9 days, such as about 7 days) wherein the total amount of vitamin B12 compound administered to the woman in any treatment period (and thus any total cycle period) does not exceed about 35 mcg, does not exceed about 30 mcg, or more particularly does not exceed 25 mcg. In one example of such an aspect, the invention provides methods that comprise administering a vitamin B12 compound, such as a natural or bioidentical methylcobalamin composition, or a composition comprising a derivative or analog thereof, for a period of only about 3-10 days, such as about 5-9 days, such as about 7 days, in each cycle of about 25-30 days, e.g., about 28 days).

In some aspects, the method of administration comprises repeating the cycle of vitamin B12 treatment period followed by a non-vitamin B12 treatment period at least two times (e.g., at least three times, at least six times, at least 12 times, at least 18 times, at least 24 times, or longer than 24 times such as even about 2-35 times, about 2-50 times, about 2-100 times, about 2-250 times, about 2-350 times, about 2-450 times, about 2-600 times, or even about 2-650 times).

According to certain embodiments, the invention provides a method of facilitating the promotion of or promoting the maintenance or restoration of blood cell levels in females experiencing a recurring vaginal discharge of blood or in females of an age that is within one or two years (before or after) a typical menstruation age. In one aspect, the female subject is at least about 12 years of age. Typically, the female subject is at least about 13-about 15 years of age and typically is at most about 50, about 55, or even about 50-60 years of age (e.g., about 14-54, about 12-60, about 12-52, about 13-55, or about 13-58 years of age).

According to certain embodiments, the invention provides a method of promoting the maintenance or restoration of blood cell levels during a recurring period associated with a physiological process, such as recurring vaginal discharge bleeding, which may be, e.g., to an otherwise normal blood cell levels in a female experiencing a recurring vaginal discharge of blood (or to an amount closer to such levels than would otherwise be the case without the treatment—such as at least about 10% more, at least about 20% more, at least about 25% more, at least about 33% more, at least about 50% more, at least about 75% more, or at least about 90% more of blood cell levels, in at least a significant number of subjects receiving such a treatment, than the level observed in such subjects not receiving the treatment).

In some aspects of the invention, the vitamin B12 compound is delivered in a pharmaceutically acceptable dosage form. In some aspects of the invention, the dosage form is administered orally. In particular aspects of the invention, the dosage form is a pharmaceutically acceptable tablet configured for oral administration.

In some aspects of the invention, the vitamin B12 compound comprises, is predominately composed of, consists essentially of, or consists of (within the limits of ordinary detection) a methylcobalamin compound, which may be a form of methylcobalamin or, e.g., a derivative or analog of methylcobalamin. In some aspects of the invention, the vitamin B12 compound is a form of either naturally sourced/occurring methylcobalamin (i.e., methylcobalamin obtained from naturally occurring sources) or bioidentical methylcobalamin, which form may be, for example, a methylcobalamin salt.

The invention also provides compositions comprising one or more vitamin B12 compound dosage forms which facilitate practicing the vitamin B12 compound administration regimens of the invention. In one aspect, the vitamin B12 compound composition is a package comprising a number of unit doses of vitamin B12 dosage forms for facilitating an intended administration regimen. In one embodiment, the dosage forms are individually packaged in the composition.

In a more particular aspect, the individually packaged dosage forms are packaged with one or more additional dosage form products that are administered on non-treatment days of a cyclic regimen of the invention. In a still further particular aspect, the additional dosage forms comprise the dosage forms that make up a triphasic hormonal birth control regimen which is taken on non-treatment days of a cyclic regimen.

DETAILED DESCRIPTION OF THE INVENTION

This disclosure describes new methods for providing one or more vitamin B12 compounds to mammals, in a more particular aspect humans, and in a still even more particular aspect female humans, and in yet even further particular aspects female humans of an age that is typically associated with menstruation. In one aspect, practicing the method serves to supplement vitamin B12 levels in a subject. In another aspect the vitamin B12 supplementation method of the invention is used to also prevent or treat/address vitamin B12 deficiency, support healthy hematopoiesis, or to provide one or more other health benefits typically associated with optimal or set target levels of vitamin B12.

The invention also provides novel compositions comprising such vitamin B12 compound supplements, which include packaged collections of dosage forms, which can alternatively be described as dosage "units", configured for administering appropriate dosages of one or more vitamin B12 compounds to such subjects in accordance with the inventive supplementation, treatment, or prevention methods described herein.

These aspects of the invention and other facets thereof will be described in further detail after a description of certain principles of construction that are intended to assist the reader in understanding the description of the invention.

Principles of Construction

Any heading(s) and sub-heading(s) provided herein (e.g., "Principles of Construction") are used for convenience only and should not be construed as limiting the invention in any way.

The use of the terms "a" and "an" and "the" and similar referents in the context of describing the invention are to be construed to cover both the singular and the plural, unless otherwise indicated herein or clearly contradicted by context.

The recitation of ranges of values in this document is intended to serve as a convenient shorthand method of referring individually to each separate value falling within the range within an order of magnitude of the endpoints of the range. For example, a recited range of 1-2 should be interpreted as disclosing 1.0, 1.1, 1.2, 1.3, 1.4, 1.5, 1.6, 1.7, 1.8, 1.9, and 2.0 and a recited range of 10-20 is to be interpreted as providing support for 10, 11, 12, 13, . . . 19, and 20). All recited ranges provided herein include the end points of the provided range, regardless of how the range is described, unless the exclusion of such endpoints is clearly stated or clearly indicated, regardless of the terminology used to describe the range. For example, a range between 1 and 5 will include 1 and 5 in addition to 2, 3, and 4 (and all numbers between such number within an order of magnitude of such endpoints, such as 1.1 and 4.9).

In some cases terms of approximation, such as "about" are used in connection with values or ranges, as a convenient way of describing a number of suitable values or where it may be difficult to precisely measure a value or limit an aspect of the invention to a particular point. Unless otherwise stated, all exact values provided herein are representative of corresponding approximate values and vice versa (e.g., all exact exemplary values provided with respect to a particular factor or measurement can be considered to also provide a corresponding approximate measurement, modified by "about," where appropriate—e.g., disclosure of "about 10" is to be understood as also providing support for 10 exactly). Ranges that are described with one or more approximate numbers should be interpreted as indicating that all endpoints and other relevant values encompassed by the range may be similarly described, regardless of any different presentations included in this disclosure (e.g., "about 10-20" should be interpreted in the same manner as "about 10-about 20"). The scope of any approximate values will depend on the context of the element at issue and the understanding of those skilled in the art (e.g., as reflected in relevant publications in the art reflecting prevailing views of ordinarily skilled persons). In the absence of typical guidance in the art, through relevant teachings or examples, the term "about" should be understood as meaning +/−10% of the indicated value(s). Other terms of approximation, such as "approximately," are to be similarly interpreted.

Use of the term "or" herein is not meant to imply that alternatives are mutually exclusive unless clearly stated or clearly contradicted by context. Thus, in this disclosure, the use of "or" means "and/or" unless expressly stated or understood by one skilled in the art. The occasional explicit use of "and/or" herein has no effect on the operation of this interpretation of "or."

All methods described herein can be performed in any suitable order unless otherwise indicated herein or otherwise clearly contradicted by context or plausibility. Unless clearly indicated or contradicted by context or plausibility, the elements of a composition disclosed herein (e.g., a pharmaceutical formulation) can be formulated in any suitable manner and by any suitable method. Unless otherwise explicitly stated or clearly contradicted by context, any combination of the various elements, steps, components, and/or features of the aspects of the invention described herein, and all possible variations thereof, is to be considered encompassed by the invention.

Numerous examples and aspects are provided in this disclosure to better illuminate the invention. No example, particular aspect, or combination or pattern thereof is intended to pose a limitation on the scope of the invention unless otherwise indicated. No language in the specification should be construed as indicating any element is essential to the practice of the invention unless as much is explicitly stated. The breadth and scope of the invention should not be limited by any of the exemplary embodiments.

Although this document provides explicit support for "means-plus-function" style interpretation of certain elements of the inventive methods and compositions, no element of this disclosure should be interpreted as indicating a "means-plus-function" construction unless such intent is clearly indicated. In particular, the use of the terms "configured to" or "adapted to" are not intended to suggest a "means-plus-function" interpretation, but, rather, typically are used to indicate that the component, composition, device, or other relevant element of this disclosure has been configured to, designed to, selected to, or adapted to achieve a certain performance, characteristic, property, or the like using the principles described herein and/or that are generally known in the art.

Use of an element or component in the singular is to be understood as also providing simultaneous disclosure and support for a plurality of the element or component, if supported or otherwise understood to be possible. For example, discussion of a vitamin B12 compound in one context should be understood as providing support for one, two, or more vitamin B12 compounds unless clearly contradicted by context or an express contradictory statement. The converse also will be understood by those of ordinary skill in the art in reading this disclosure. In other words, the singular is intended to convey the plural and vice versa herein, unless otherwise stated or clearly contradicted by context.

The description herein of any aspect or embodiment of the invention using terms such as "comprising" with reference to an element, composition, or set of compositions or elements should be interpreted, whether explicitly stated or not, as simultaneously providing support for a similar aspect or embodiment of the invention that "consists of", "substantially comprises" (is at least about 5% composed of), "predominately comprises" (is detectably greater than 50% composed of), and "substantially consists of" (is at least about 90% composed of) that particular element, unless otherwise stated or clearly contradicted by context (i.e., a composition described herein as comprising a particular element should be understood as also describing a composition consisting of that element, substantially comprising that element, predominately comprising that element, and substantially consisting of that element, unless otherwise stated or clearly contradicted by context). Terms such as "including", "containing", and "having" should otherwise be interpreted openly herein, e.g., as meaning "including, but not limited to", "including, without limitation", or "comprising", unless otherwise such a meaning is clearly contradicted. The phrase "detectably or significantly" is used to describe a result that is measurable (detectable) or statistically significant as determined by an appropriate test in the given context (e.g., using a p≤0.05/0.01 test if appropriate).

Changes to tense or presentation of phrases defined herein (e.g., using "comprises predominately" instead of "predominately comprises") will not modify the meaning of the defined phrase, unless otherwise clearly indicated.

All references, including publications, patent applications, and patents, cited herein, including any patents and patent applications that may be cited above such as in the Background of the Invention, are hereby incorporated by reference to the same extent as if each reference were individually and specifically indicated to be incorporated by reference and were set forth in its entirety herein. Accordingly, the reader should review and consider such references in understanding the full content of this disclosure. For example, unless clearly contradicted by context or explicit statement, the disclosure of such documents relating to formulations, methods of production, and methods of use of compositions and devices can be combined with the teachings provided herein to provide additional useful compositions and applications. However, the reader should understand that the citation and incorporation of patent documents herein is limited to the technical disclosure of such patent documents and does not reflect any view of the validity, patentability, and/or enforceability of any claims of such patent documents. Moreover, in the event of any conflict between this disclosure and the teachings of such documents, the content of this disclosure will control with respect to properly understanding the various aspects of the invention.

Unless clearly indicated, the scope of any aspect or embodiment of the invention is not limited to particular processes, compositions, or methodologies described, as these can vary. The terminology used in the description is for the purpose of describing particular versions or embodiments only; and is not intended to limit the scope of the invention. Unless defined otherwise, all technical and scientific terms used herein have the same meanings as commonly understood by one of ordinary skill in the art and should be interpreted broadly. In general, any methods and materials similar or equivalent to those described herein can be used in the practice or testing of embodiments of the invention, the methods, devices, and materials described herein.

Vitamin B Compounds and Vitamin B Compositions

Methods of the invention described in this disclosure comprise administering one or more vitamin B12 compounds, typically contained in one or more vitamin B compound compositions, which vitamin B compound compositions may be contained in or made part of a physiological acceptable dosage form (e.g., a dosage form additionally comprising one or more carriers, excipients, and the like), to a mammalian subject (e.g., a human female that experiences recurring vaginal bleeding discharge). In general, the methods of the invention can be practiced with any suitable vitamin B12 compound, though in particular aspects the vitamin B12 compound is one of the currently leading vitamin B12 supplements, a form of vitamin B12 endogenously found in humans, or both (as in the case of methylcobalamin).

A "vitamin B12 compound" in this disclosure means any compound (a) having a structure of the cobalamin group or that has a substantially similar structure (e.g., a structure that is at least about 80%, at least about 85%, at least about 90%, at least about 92.5%, at least about 95%, or at least about 97.5% identical in its atoms, atomic arrangement, and bonding to the cobalamin structure), (b) is pharmaceutically/nutritionally suitable (i.e., safe for administration to the intended subject or subject population in relevant doses), and (c) results in one or more vitamin B12 like physiological effects (e.g., nutritional or pharmaceutical effects) when administered at sufficient dosage(s) over a sufficient treatment period, particularly in accordance with one or more administration regimens described further in this disclosure.

Vitamin B12 effects of any compound (or lack thereof) can be evaluated by comparison with the administration of a corresponding or similar amount of methylcobalamin or another recognized form of vitamin B12 using any suitable test for the effect(s) of interest (e.g., blood cell counting methods). A vitamin B12 effect of a vitamin B12 compound can be an effect of lesser or greater magnitude than a corresponding effect associated with an identical or similar amount of methylcobalamin level or administration. For example, a physiological effect associated with a vitamin B12 compound that is at least about 50%, at least about 75%, or at least about 90% as great as the effect in a corresponding or similar amount of methylcobalamin still can be a suitable vitamin B12 effect. An effect of administering a vitamin B12 compound that is at least 1.25 times as great, at least about 1.5 times as great, at least about 2 times as great (i.e., at least double), or even at least about 3 times as great (i.e., at least about triple) than the corresponding effect associated with a corresponding level or administration amount of methylcobalamin or other form of vitamin B12 also can be a suitable vitamin B12 effect. Typically, a vitamin B12 compound also will exhibit some, most, or all of the major physiochemical properties of typical forms of vitamin B12, such as methylcobalamin, which physicochemical properties are known in the art or can be determined through application of routine analytical methods.

Cobalamins are compounds having the base molecular formula of C63H88CoN14O14P and the structure shown in Compound 1 below (wherein R is any suitable atom or compound, such as an —OH, -methyl (-Me), or an organic moiety comprising one or more rings, heteroatoms, or combination thereof)—

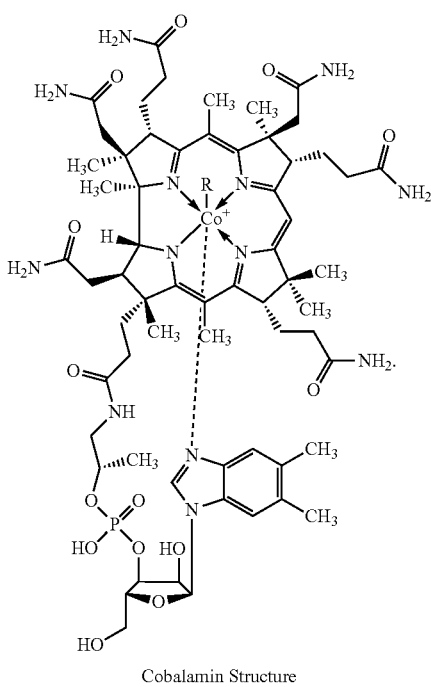

Compound 1

Cobalamin Structure

Vitamin B12 compounds of the invention can have a cobalamin structure or a cobalamin-like structure (such as an analogous structure, such that the compound can be described as a cobalamin "analog," or a derivatized structure, such that the compound can be described as a "derivative" of a cobalamin or cobalamin analog).

An "analog" is a compound in which one or more of the atoms of a referenced compound or structure (e.g., the cobalamin structure) is removed (absent) or substituted with a suitable replacement atom, typically without significantly detracting from the desired nutritional or pharmaceutical properties of the referenced ("parent") compound, and without rendering the analog unsafe or otherwise unsuitable for use. Typically, no more than about 15, no more than about 10, no more than about 7, no more than about 5 of the atoms or bonds in a cobalamin analog will differ from those in the structure shown in Compound. 1, above. In certain aspects, an analog will only have 1, 2, 3, or 4 deletions or additions of atoms or bonds. In some aspects an analog can be a deuterated analog, or comprise other substitutions, such as carbon-to-boron substitutions. Analogs within the scope of the term "vitamin B12 compound" can be developed or identified through use of routine experimentation without undue burden to those of ordinary skill in the art.

A "derivative" is a compound comprising a referenced compound or structure (e.g., a cobalamin core or a cobalamin analog core), but in which one or more atoms or groups (moiety(ies)) have been added to the compound, typically without changing the basic pharmaceutical/nutritional suitability of the compound and without significantly impairing the vitamin B12 function of the compound and overall safety and suitability of the compound, although it is understood that derivatized compounds which can be generated without undue experimentation often can impart desired functionalities with respect to an un-derivatized counterpart (parent compound), such as longer half-life, traceability, and the like.

Vitamin B12 compounds also can comprise alternative forms of a compound, analog, or derivative, such as a different suitable salt form, a hydrate, a solvate, an isomer, or a polymorph thereof.

Various forms of vitamin B12 compounds that are suitable for consumption by humans are known in the art and the structure and properties of such compounds can be readily used to design and generate analogs or derivatives and the properties of such compounds can be used to select nutritionally/pharmaceutically acceptable analogs, derivatives, and alternative forms of vitamin B12 compounds having desirable health effects or activity without undue experimentation.

According to certain embodiments, a Vitamin B12 compound can be a cobalamin molecule with an additional molecule or group attached to the cobalt at its core. According to some aspects, such a molecule could be any molecule or group yielding a pharmaceutically acceptable compound. Exemplary molecules or groups that can be attached to the core of such a compound can include but not be limited to a cyanide molecule, a methyl group, a hydroxy group, or a nitro group. The resulting cobalamin compounds can be synthetic or naturally occurring cobalamin compounds. According to some aspects, exemplary cobalamin molecules include the addition of a hydroxy group to form hydroxocobalamin or a nitro group to form a nitrocobalamin. According to certain embodiments, exemplary cobalamin molecules can include the addition of a cyanide molecule to form cyanocobalamin (a synthetic form of cobalamin that is one of the two leading forms of vitamin B12 used in leading supplement formulations), or a methyl group to form methylcobalamin (a naturally occurring form of a cobalamin compound and the other of the two major forms of vitamin B12 used in leading supplement formulations). Structures for these respective compounds are shown in Compound 2 and Compound 3, below:

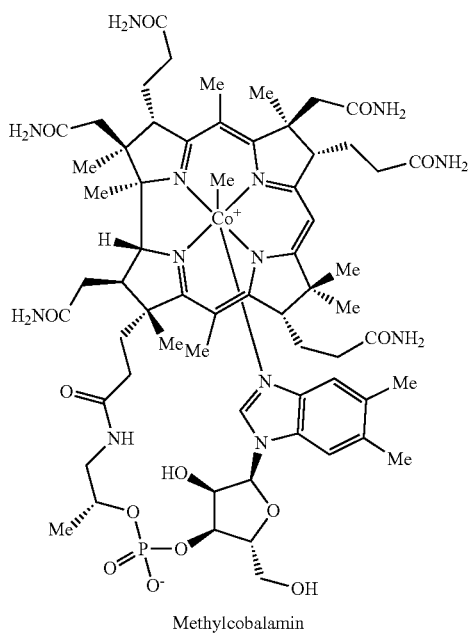

Compound 2

Methylcobalamin

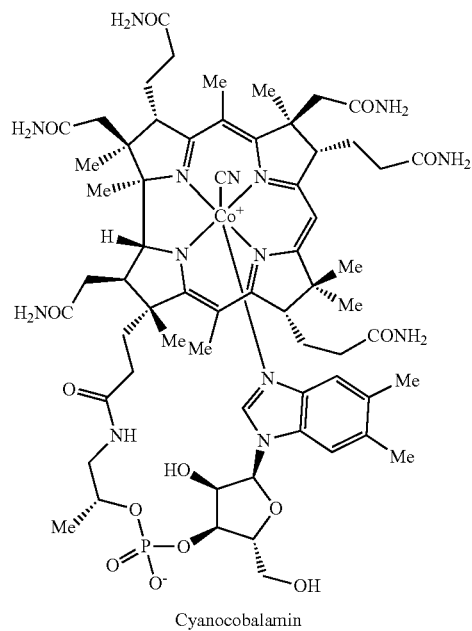

Compound 3

Cyanocobalamin

Other similarly modified cobalamins can include but may not be limited to glutathionylcobalamin and sulfitocobalamin, among others. In some aspects of the invention, the cobalamin compound can be an adenosylcobalamin. Like methylcobalamin, adenosylcobalamin is an enzymatically active form of vitamin B12 that occurs naturally (most of a human's reserves of vitamin B12 are stored as adenosylcobalamin and converted to methylcobalamin as needed by the body).

In one aspect, the vitamin B12 compound is an analog or a derivative of methylcobalamin or another one of the above-described specific cobalamin compounds.

According to other embodiments, the vitamin B12 compound can be or can be substituted in any of the various methods and compositions described herein with one or more compounds that are precursors, prodrugs, or active metabolites of one or more forms of vitamin B12 or any other compound that is capable of releasing, forming, or otherwise enhancing the amount or activity of vitamin B12 or such a related compound in vivo, so long as such compounds ultimately exhibit sufficiently similar in vivo functionality as vitamin B12 (e.g., as discussed above in connection with analogs and derivatives), in particular in terms of the ability to cause vitamin B12 effects, such as to alleviate symptoms of vitamin B12 deficiency or to promote or enhance hematopoiesis, and are otherwise safe and suitable for the practice of the relevant target administration regimen.

It will be clear from the foregoing that in many aspects of the invention, the vitamin B12 compounds of the invention can comprise (a) any vitamin B12 compound, such as any suitable analog, derivative, or form, (b) any vitamin B12-related compound, such as precursor/prodrug or metabolite of a naturally occurring or leading supplement synthetic form of vitamin B12, or (c) any suitable combination thereof, so long as the vitamin B12 compound/related compound is capable of demonstrating the same, better, or at least reasonably comparable activity in vivo as one or more forms of vitamin B12, e.g., in terms of the ability of the compound to alleviate symptoms of vitamin B12 deficiency or to promote hematopoiesis.

As noted elsewhere, in certain aspects, vitamin B12 compounds can comprise either a cobalamin compound or an analog or derivative thereof (or a derivative of an analog thereof). In common embodiments, the vitamin B12 compounds of the invention are selected from the group comprising cobalt corrinoids of the cobalamin group, which include in particular, cyanocobalamin, hydroxocobalamin, methylcobalamin, and nitrocobalamin.

According to even more particular embodiments, the vitamin B12 compound of the dosage form(s) and methods of the invention comprises, predominately comprises, consists essentially of, or consists of a methylcobalamin compound or an analog thereof (e.g., an analog of methylcobalamin comprising one, two, three, four, or five substitutions or deletions of atoms or bonds occurring in naturally occurring methylcobalamin) or derivative thereof (e.g., a derivative of methylcobalamin comprising one, two, three, four, or five additional atoms or moieties as compared to methylcobalamin), or an alternative form of any thereof including a salt, prodrug, hydrate, solvate, polymorph, or deuterated form of methylcobalamin. In some aspects, the vitamin B12 compound is a salt of a methylcobalamin compound, such as a salt of a naturally sourced methylcobalamin or a suitable salt of a bioidentical methylcobalamin compound (a "bioidentical compound" is a synthetic compound that is identical in structure and composition to a naturally occurring and naturally sourced compound; a "naturally sourced compound" is a compound obtained from natural sources, such as naturally occurring organisms).

In general, any of the methods, compositions, and principles described above and elsewhere herein with respect to vitamin B12/cobalamin compositions, generally, can also be applied to any of the more particular exemplary compounds and classes of compounds specifically recited herein, and uses thereof, such as methylcobalamin compounds, and vice versa, and the disclosure herein should be interpreted accordingly, but without disregarding the particular properties of such specific compounds and classes as compared to such broader classes of compounds.

In many aspects the vitamin B12 compound is a methylcobalamin compound. In numerous aspects, the vitamin B12 compound is naturally occurring methylcobalamin, which can be naturally sourced methylcobalamin or a bioidentical methylcobalamin or a suitable form of either thereof (e.g., a pharmaceutically acceptable salt thereof). In any case in which a vitamin B12 compound is described herein, it should be understood that the use of such compounds specifically is also contemplated. To emphasize this point such compounds will be specifically mentioned in connection with several disclosures that reference the broader class of vitamin B12 compounds herein, but the lack of any specific mention of such particular methylcobalamin compounds in any other part of this disclosure should not be interpreted as indicating that the use of such specific compounds is not also implicitly provided by such broader disclosure, except where explicitly indicated.

A "vitamin B12 compound composition" (sometimes referred to as a vitamin B12 composition) is any suitable composition that comprises one or more vitamin B12 compounds, typically in an amount or amounts that is/are sufficient for inducing, promoting, modulating, or causing the desired pharmaceutical or nutritional effect of the composition when administered according to one of the methods of the invention. One type of vitamin B12 compound composition is a dosage form; types and examples of which are described in detail further herein. Another type of vitamin B12 compound composition is can be classified as an "intermediate composition" containing the vitamin B12 compound(s), but which is not considered in final form for optimal administration. Typically, an intermediate composition will be mixed with one or more excipients, fillers, and the like, to form a vitamin B12 compound dosage form. In this respect, an intermediate composition usually means a composition that comprises a vitamin B12 compound and one or more other ingredients and typically acts as a source of vitamin B12 for a dosage form formulation.

A vitamin B12 compound composition can comprise a vitamin B12 compound (or combination thereof) as the sole active pharmaceutical/nutritional agent(s) of the vitamin B12 compound composition. In another aspect, the methods of the invention can lack the administration of any pharmaceutical or nutritional ingredients during the period in which the vitamin B12 is administered that cause vitamin B12 effects.

In another facet, the vitamin B12 compound/compounds of any vitamin B12 composition is present in combination with one or more additional active agents. In other aspects, the vitamin B12 compound is also or alternatively administered with one or more additional active agents ("actives"). Such additional "actives" can be any active ingredient promoting any suitable and desired health effect, including the treatment or prevention of various conditions. In one aspect, the additional active is able to also promote or cause the alleviation of vitamin B12 deficiency symptoms; detectably promote, cause, or support hematopoiesis; or cause both types of such effects. In other aspects, the one or more additional actives are capable of modulating the reproductive cycle (e.g., regulating ovulation or otherwise acting as a birth control agent), regulating other health conditions, or promoting positive general health. Usually any additional active making up part of a composition or method herein does not significantly or, typically even detectably, compromise or significantly compromise (e.g., compromise by any more than about 33%, more than about 20%, more than about 10%, more than about 5%, or even more than about 1%) the average/expected efficacy(ies)/effect(s) of the vitamin B12 compound in a mixed vitamin B12 composition or of the vitamin B12 compound that is also administered as part of a method of the invention (together or separately, the latter as in the case of a cyclic regimen).

Also or alternatively, according to other aspects of the invention the vitamin B12 compound in a vitamin B12 composition (e.g., in a vitamin B12 composition dosage form), does not significantly or, typically even detectably, compromise or significantly compromise (e.g., compromise by any more than about 5%, more than about 4%, more than about 3%, more than about 2%, more than about 1%, more than about 0.5%, more than about 0.4%, more than about 0.3%, more than about 0.2%, more than about 0.1% or even less) the desired efficacy(ies)/effect(s) of any one or more of the one or more additional actives present as part of a method of the invention (e.g., a hormonal birth control drug).

According to specific embodiments, the vitamin B12 compound or vitamin B12 compound dosage form present or administered with otherwise in relation to the administration of one or more additional actives or supplements (e.g., a pharmaceutical treatment regimen that regulates ovulation, such as for example a triphasic birth control regimen), does not lead to any statistically significant change in the safety profile of the associated pharmaceutical treatment regimen (e.g., by significantly increasing the incidence of any adverse events associated with the associated other actives or supplements). In such aspects, the co-administration, overlapping administration, or otherwise related administration of the vitamin B12 compound(s) and such other actives or supplements are not expected to result in the formation of deleterious reactants, cause adverse reactions, or cross-interfere with each other before or after administration.

In another aspect, the safety of the one or more actives used as part of a method of the invention will typically not significantly impact, and desirably not be detectably impact, any aspect of the associated vitamin B12 dosage form (in terms of efficacy, nutritional properties, or safety).

In another aspect, neither the vitamin B12 compound, nor the vitamin B12 compound dosage form, nor any other active or supplement administered as part of one of the methods described herein, are independently or together associated with a significantly increased risk of developing cancer (e.g., as may be determined by relevant preclinical and/or clinical studies, such as one or more studies that each would be classifiable as well-controlled and adequate studies with respect to submission to leading regulatory agencies such as US FDA).

In certain aspects, one or more additional actives delivered with the vitamin B12 compound(s) or in connection with the administration of the vitamin B12 compounds (such as being administered on non-treatment days in a cyclic treatment regimen) are selected from a group comprising one or more additional vitamins, one or more minerals, one or more compounds that may have "nutraceutical" properties (e.g., an omega-3 fatty acid, a flavonoid, a prebiotic, a probiotic, a nutritional antioxidant, a fiber, and the like); or one or more active pharmaceutical ingredients ("APIs"), such as an antibiotic, a drug to treat the symptoms of menstrual cramping or discomfort, and the like; or any other pharmaceutically and physiologically acceptable molecules or compounds which does not substantially or detectably interfere with the activity of the vitamin B12 compound in achieving desired vitamin B12 effects, such as alleviating vitamin B12 deficiency, promoting the detectable or significant restoration or maintenance of a healthy blood cell population, or providing any other desired vitamin B12 effect.

According to certain embodiments, compositions or methods of the invention will comprise one or more additional vitamins or minerals in combination with the vitamin B12 compound or vitamin B12 compounds of such compositions or methods. In some aspects of the invention, the additional compound can be another B vitamin. In some aspects, the additional B vitamin can be folic acid.

According to certain embodiments, the vitamin B12 compound oral dosage form can also or alternatively additionally comprise one or more minerals. According to certain embodiments, the one or more additional minerals is a physiologically suitable form of iron. Other minerals that can be co-administered or co-formulated can include magnesium, calcium, zinc, or a combination of any or all thereof.

In some embodiments, the vitamin B12 compound composition or method additionally comprises a vitamin B12 compound, folic acid, iron, or a combination of some or all thereof (e.g., one or more vitamin B12 compounds with folic acid, iron, or both folic acid and iron).

According to embodiments, additional vitamins or minerals delivered with the vitamin B12 compounds or co-contained/co-formulated with the vitamin B12 compounds in a vitamin B12 compound composition are present or delivered in an amount corresponding to at least about 25%, at least about 33%, at least about 50%, at least about 66%, or at least about 90%, such as at least about 125%, at least about 150%, at least about 200%, or even at least about 300% of the recommended daily intake ("RDI") for such vitamins and/or minerals (according to official or prevailing nutritional standards in the United States, European Union, Japan, China, India, or a combination of any or all thereof).

In certain embodiments, the invention provides methods comprising administering a vitamin B12 compound composition to the subject in which the composition does not comprise any additional vitamins (or significant amount of any additional vitamins—such as more than about 0.1 mcg, more than about 0.25 mcg, more than about 0.5 mcg, more than about 1 mcg, or more than about 2 mcg of any such additional vitamin). In other aspects of the invention, the vitamin B12 compound composition also or alternatively lacks any additional minerals or lacks any significant amount of any additional mineral (e.g., at the amounts described in the preceding sentence with respect to additional vitamins). In certain embodiments, the vitamin B12 compound/dosage form or methods do not comprise any amount or at least do not comprise any significant amount of folic acid. In some aspects the vitamin B12 compound composition does not include a nutritionally/therapeutically significant amount of folic acid (e.g., any more than about 10%, about 20%, or about 30% of the recommended daily intake ("RDI") thereof). In certain embodiments, the vitamin B12 compound composition or method similarly does not comprise iron or does not comprise significant amounts or nutritionally/therapeutically relevant amounts of iron. According to certain aspects, the vitamin B12 compound composition or method does not comprise either folic acid or iron or any significant or therapeutically/nutritionally relevant amounts of folic acid and iron.

In particular aspects of the invention, the primary, exclusive, or essentially/substantially exclusive form of the vitamin B12 compound in the vitamin B12 compound composition is limited to one or more methylcobalamin compounds, and typically the vitamin B12 compound will be limited to or essentially limited to (i.e., substantially consists of or essentially consists of) a single form of a methylcobalamin compound.

According to certain embodiments, a methylcobalamin compound is incorporated into (discretely or non-discretely) or otherwise contained in the vitamin B12 dosage form to be administered to the subject as a component of a more complex added ingredient (i.e., an intermediate composition). The methylcobalamin can be incorporated into the vitamin B12 compound dosage form as a component of any added ingredient wherein the remainder of the intermediate composition/ingredient is nutritionally or pharmaceutically acceptable and does not significantly or detectably inhibit the desired functionality of the vitamin B12 compound (e.g., in alleviating vitamin B12 deficiency symptoms or promoting healthy hematopoiesis). Incorporation of the vitamin B12 compound as an ingredient of another composition can be helpful (e.g., in handling or stability) when small amounts, e.g. low concentrations, of an ingredient are required, or when the vitamin B12 compound is normally contained in such an intermediate composition. According to certain embodiments, a methylcobalamin compound of a vitamin B12 compound dosage form is incorporated into the dosage form as an ingredient of a composition that substantially comprises, predominately comprises, or substantially consists of a dicalcium phosphate composition. The methylcobalamin compound in such aspects can be present within (i.e., as part of) the dicalcium phosphate composition in any amount suitable for providing the target amount methylcobalamin in a desired dosage form.

The amount of vitamin B12/cobalamin compound contained in a composition to be added as a component to the vitamin B12 compound dosage form of the invention can be any suitable amount for carrying out the particular method of the invention. A suitable amount will vary with the intended dosage form and dosage regimen used in the intended method to be associated with the ingredient composition. Similarly, the one or more vitamin B12/cobalamin compounds of the ingredient composition can be present in any suitable concentration, depending upon, inter alia, the relative vitamin B12 compound concentration.

According to certain exemplary aspects, a vitamin B12 compound, such as a methylcobalamin compound (e.g., natural or bioidentical methylcobalamin) will make up about 0.25%-2% of a methylcobalamin ingredient composition (e.g., an intermediate composition, a dosage form, or both), such as between about 0.5% and about 1.75% of the methylcobalamin composition, such as between about 0.75% and about 1.5% of the methylcobalamin ingredient composition. According to certain aspects, the vitamin B12 compound, such as a methylcobalamin compound, is present in a dosage form to be used in methods of the invention in a concentration of about 0.1 wt. % to about 0.4 wt. %, such as about 0.15 wt. % to about 0.35 wt. %, e.g., about 0.2-0.3 wt. %, e.g., about 0.225-0.275 wt. % or about 0.25 wt. % (e.g., 0.24 wt. %).

Administration, Dosages, and Dosing Regimens/Therapeutic and Nutritional Applications The various methods of the invention comprise administering one or more vitamin B12 compounds, typically contained in one or more vitamin B compound compositions, which vitamin B compound compositions may be contained in or made part of one or more physiological acceptable dosage form(s) (e.g., a dosage form comprising one or more carriers, excipients, and the like), to a mammalian subject.

While the mammalian subject can be a non-human mammal of any sex (such as a primate, a companion animal, or the like), the subject usually is a female or usually a human, and commonly a female human. In typical aspects the subject is a human female that is or would be undergoing menstruation if not subject to a condition or treatment that inhibits menstruation, such as a hormonal birth control method or other method of controlling ovulation or menstruation.

In one aspect the vitamin B12 supplementation methods of this invention are used to prevent or treat/address vitamin B12 deficiency, support healthy hematopoiesis, or to provide one or more other health benefits associated with vitamin B12 (i.e., to modulate one or more vitamin B12-related conditions). In this respect, the term "treat" herein means to detectably change one or more physiological symptoms or underlying causes of a referenced condition and by doing so to detectably reduce, ameliorate, or improvably change such cause or symptom (e.g., by reducing the severity, spread, duration, frequency, or degree thereof). The term "prevent" means to reduce the likelihood of a condition occurring or to reduce the duration, severity, spread, or frequency of recurrence of one or more referenced conditions. "Treatment" and "prevention" typically mean that the practice of the method has been determined to be associated with scientific evidence of such aspects of treatment or prevention in a relevant number of similar subjects as the subject the method is performed on, such as by demonstration of a statistically significant result in one or more (e.g., two or more) well-controlled and adequate clinical studies. Treatment or prevention also can mean or, less often, alternatively can mean, treatment or preventing a condition in an individual subject. While both forms of these two terms should be considered to be provided by any use of these terms in this disclosure, the first interpretation (i.e., that the method is supported by scientific evidence of the efficacy of such treatment or prevention has been established) should be used in understanding the scope of any particular claim or aspect of this disclosure unless the alternative interpretation is clearly indicated.

In another aspect of the invention the administration of the vitamin B12 compound is simply performed as a method of dietary supplementation of vitamin B12 levels in a subject, regardless of whether or not such level of supplementation has been shown to treat or prevent any particular disease or condition. It should be understood that any methods described herein for treatment or prevention of conditions can also be performed simply as methods for supplementing vitamin B12 levels in a subject. In certain aspects, the vitamin B12 compound used in such methods is one that could readily be classified as "generally recognized as safe" (i.e., be considered "GRAS" or to have GRAS status, according to regulatory standards, such as US FDA standards).

In particular aspects, methods of the invention comprise administering a vitamin B12 compound-containing dosage form for promoting of one or more vitamin B12-effects, such as replenishment or maintenance of healthy blood cell levels in a mammal (e.g., in a female that often or regularly experiences menstruation or breakthrough bleeding). The term "promoting" in this respect and similar contexts of this disclosure means detectably or significantly increasing the effect, the timing to an effect occurring, or likelihood of the effect occurring, or increasing the magnitude, duration, or spread of the effect in the individual upon occurring, or, more typically, demonstrating any thereof in a class of similar individuals as a statistically significant effect in a scientific study, such as a well-controlled and adequate clinical trial, such that such promotion of the effect in the individual has a reasonable chance of occurring upon a similar level and manner of administration of a similar dosage form.

The vitamin B12 compounds are in one aspect of the invention administered to female subjects, typically menstruating female human subjects or those experiencing breakthrough bleeding while on a hormonal birth control method, so as to supplement vitamin B12 levels in the subject; to promote health, nutrition; or to induce, promote, or cause (or to facilitate the inducement, promotion, or cause) of one or more physiological effects in the subject, such as the generation of red blood cells.

The amount of vitamin B12 compound, composition, or both, administered to the subject in any of the various methods described herein can be described as a "dose." A dose can refer to both an individual dose, which typically is a dosage given 1 or 2 times a day (usually once daily), or the total dose of the dosage form administered to the subject for a period or cycle. Even where not so differentiated the particular meaning of any use of the term "dose" in this disclosure will typically be clear to those of ordinary skill in the art based on the context of use.

An administration plan comprising the administration of one or more doses, and any breaks in dosing, can be described as a "dosing regimen" or "treatment regimen." Methods of the invention include a variety of dosing regimens, as will be further exemplified below.

According to certain embodiments, the dosing regimen can be described as a non-continuous or intermittent treatment regimen. That is, in some aspects, the vitamin B12 compound dosage is administered only for a period of treatment having a defined length of time, such as 14 days or less, 12 days or less, 11 days or less, or 10 days or less, such as less than 9 days, less than about 8 days, less than 7 days, less than 6 days, less than 5 days, or less than about 4 days (e.g., 1, 2, or 3 days). In some embodiments, the vitamin B12 compound dosage treatment period of such an intermittent treatment regimen can comprise a treatment period of between about 1-15 days, such as for example between about 2-12 days, or for example, between about 3-10 days. Usually the treatment period is a part of a longer period of time, and often the treatment period is a recurring part of a recurring longer period that defines a cycle. According to certain embodiments the vitamin B12 compound dosage form is not administered on non-treatment days of the associated total period or cycle.

In some aspects of the invention, the vitamin B12 compound dosage treatment period can be a period of between about 3-10 days (e.g., about 7 days) out of every approximately 30-day period (e.g., every 28 days).

According to certain embodiments, the vitamin B12 dosage forms of the invention can be administered during a treatment period representative of about 8-40% of a month (or 4-week period), such as for example between about 8% and about 40% of any single month period, such as for example between about 10% and about 40%, between about 15% and about 40%, between about 20 and about 40%, between about 25% and about 40%, between about 30% and about 40%, between about 35 and about 40%, such as for example between about 10% and about 35%, between about 10% and about 30%, between about 15% and about 30%, between about 20% and about 25%, for example between about 15% and about 35% or for example between about 20% and about 30% of an approximately 4-week period.

According to certain embodiments of the invention, the vitamin B12 compound dosage form administration days are expected to correlate with the period of time in a human female subject's reproductive cycle in which blood loss occurs. Such blood loss days (the female's period or period of breakthrough bleeding) can be approximately 12 days in length, such as for example about 11 days in length, about 10 days in length, about 9 days in length, about 8 days in length, about 7 days in length, about 6 days in length, or about 5 days in length, such as for example approximately 4 days in length, approximately 3 days in length, approximately 2 days in length, or for example a single day in length, depending on, e.g., whether the women is subject of any treatments that regulate the period and other conditions. Such blood loss can be through menstruation or breakthrough bleeding (e.g., as experienced by those subscribing to a birth control method).

In one aspect the invention provides a method of vitamin B12 supplementation, such as a non-continuous, e.g., cyclic supplementation regimen, comprising administering a vitamin B12 compound composition to a female on only certain day of a recurring period, such as a period in which a female subject is expected to experience a recurring vaginal discharge of blood or tissue. Such a recurring vaginal discharge can comprise the natural discharge of the uterine lining, which can include both tissue and blood loss (phrases such as "vaginal discharge of blood" herein are intended to encompass recurring loss of blood and/or recurring loss of tissue such as may be associated with menstruation as well as any breakthrough bleeding or spotting which can occur in women either taking or not taking hormonal birth control methods).

According to certain embodiments, the administration of the vitamin B12 compound dosage forms of the invention takes place during the expected bleeding days of a monthly reproductive cycle. According to alternative embodiments, the administration of the vitamin B12 compound dosage forms of the invention takes place during the breakthrough bleeding days of a cycle of a woman using a hormonal contraceptive method.

In some aspects, the vitamin B12 compound dosage form of the invention can be administered on days when blood loss occurs, such as for example on days when a human female subject experiences vaginal discharge of blood.

According to alternative aspects, the vitamin B12 compound dosage form of the invention can be administered on days when no blood loss occurs.

According to yet further alternative embodiments, a vitamin B12 compound dosage form treatment period can span a period of time incorporating days when some blood loss occurs and some days where no blood loss occurs.

In alternative embodiments, a continuous vitamin B12 supplementation regimen is provided, wherein the total amount of vitamin B12 compound (e.g., methylcobalamin) administered to the subject in any month of use is about 150 mcg or less, about 125 mcg or less, about 100 mcg or less, about 90 mcg or less, or about 80 mcg or less (e.g., about 75 mcg). In such aspects of the invention, a vitamin B12 compound dosage form can be administered daily, without any therapeutically significant interruptions in administration throughout the entire period in which vitamin B12 supplement is provided to the subject, as is described elsewhere herein (e.g., over a period of at least 3 months, at least 6 months, at least 9 months, at least 12 months, at least 18 months, at least 2 years, at least 3 years, at least 5 years, or longer).

The vitamin B12 compound dosage forms of the invention can be administered alone (as the sole treatment provided during vitamin B12 compound treatment days of the regimen). In some aspects of the invention, the vitamin B12 compound dosage form is administered without the co-administration of any other pharmaceutically active compound, nutritional supplement, or both. In some aspects, such other pharmaceutical or nutritional products can be administered to the subject, but only or at least substantially only on non-treatment/supplementation days (i.e., those days of the total period or cycle in which the vitamin B12 compound is not administered).

In certain embodiments, the vitamin B12 compound dosage form is administered in conjunction with one or more additional nutritional supplements, drugs, or therapeutic methods, such as with one or more additional oral dosage form(s) comprising one or more compounds, compositions, or actives.

In some aspects of the invention, an additional dosage form can be an additional orally administered dosage form. In some embodiments, the one or more additional dosage forms comprise(s) a vitamin B compound, which may be a vitamin B12 compound or another vitamin B compound, such as folic acid. In some embodiments the one or more additional dosage forms does not comprise a vitamin B12 compound. In certain aspects, the one or more additional dosage form(s) can comprise an active in the form of one or more of a nutritional supplement, a nutraceutical, or a pharmaceutical drug. The one or more additional dosage forms generally can comprise any compound, composition, or formulation which does not inhibit the desired impact of administering the vitamin B12 compound dosage form (e.g., in supplementing vitamin B12 levels or alleviating one or more symptoms of vitamin B12 deficiency; or promoting hematopoiesis).

According to specific aspects of the invention, one or more additional dosage forms comprising one or more actives can be also or alternatively co-administered with a vitamin B12 compound dosage form.

According to alternative aspects, the one or more additional oral dosage forms comprising one or more actives can be administered during a period of time wherein a vitamin B12 compound dosage form is not administered.

According to certain embodiments, the one or more actives can be administered during a period of a human female subject's monthly reproductive cycle wherein a vitamin B12 compound dosage form of the invention is not administered. Such a period of time can be when no recurring vaginal bleeding is expected.

In some embodiments a vitamin B12 compound composition, such as an oral dosage form comprising a methylcobalamin compound, is administered during the expected bleeding phase of a woman's cycle and a second oral dosage form is administered on all other days (or essentially all other days) of a woman's cycle and such second oral dosage form does not contain a vitamin B12 compound. The second oral dosage form can be a placebo compound lacking any active pharmaceutical ingredients or supplements (e.g., a sugar pill), or, according to other aspects, the second oral dosage form can comprise one or more pharmaceutically active or nutritional ingredients.

The one or more other active dosage forms can comprise any suitable one or more actives beneficial to the health of the subject (i.e., that are safe and that do not substantially interfere with the effect of the vitamin B12 compound of the invention). For example, the subject can be a menstruating woman, a subject taking a hormonally controlled contraceptive or hormone replacement therapy, a subject undergoing chemotherapy, or other such subject receiving or taking a prescribed or non-prescribed dosage form for a defined period of time. According to certain embodiments, the one or more other active dosage forms can be other B vitamins such as but not limited to folic acid or vitamin B6, other hematopoiesis-promoting elements such as iron, a prescribed drug such as a chemotherapeutic agent, a fertility drug, a contraceptive agent, or any other pharmaceutically acceptable and physiologically beneficial pharmaceutical ingredient or supplement.

According to some aspects, the one or more other active dosage forms can be a steroid drug. In some embodiments the steroid drug can be any steroid promoting the health and/or wellness of a participant, such as for example a corticosteroid or an anabolic-androgenic steroid. In some aspects the steroid drug is an orally administered steroid drug. According to some aspects, the one or more other active dosage forms can comprise a steroid hormone. In some aspects, the steroid hormone or other steroid drug is a steroid product that has been credibly determined to directly or indirectly detectably decrease the levels of vitamin B12 in subjects or in the subject after a period of administration.

One or more other active dosage forms administered with the vitamin B12 compound dosage form of the invention or administered during non-treatment periods of vitamin B12 compound dosage form wherein no vitamin B12 is administered could be any steroid hormone, such as one or more steroid hormones used for hormone replacement therapy, prevention of pregnancy (e.g. an ovulation-inhibiting contraceptive), regulation of a menstruation cycle, enhancement of fertility, suppression of symptoms of hypogonadism, reduction of menstruation symptoms and/or reduction of the amount of blood loss during menstruation.

According to certain embodiments, steroid actives present in the one or more other active dosage forms can be a steroid hormone such as a steroid selected from the group consisting of estrogens, progestogens, or both.

As used herein, a "progestogen" is any molecule capable of binding to a progesterone receptor and can comprise a progestin (a synthetic progestogen) or a naturally occurring progestogen. According to some embodiments, an estrogen administered as an additional active can contribute to the regulation of conception. According to some embodiments, a progestogen can similarly contribute to the regulation of conception. According to some embodiments, a combination of an estrogen and a progestogen can contribute to the regulation of conception. In some aspects of the invention, the estrogen, the progestogen, or both the estrogen and the progestogen can be a pharmaceutically active ingredient of the one or more other active dosage forms.

In aspects, at least one of the conception-regulating pharmaceutically acceptable ingredients comprises an estrogen receptor modulating compound. According to certain embodiments, incorporated estrogens of the one or more other active dosage forms can be any form of estrogen that is capable of releasing such an estrogen in vivo or modulating the activity of an estrogen receptor. Such compounds can be considered "estrogen receptor modulating means" where a means-plus-function description of such an inventive method is desired. For example, in some aspects an estrogen present in another active dosage form can include but not be limited to ethinyl estradiol ("EE"), 17-beta-estradiol, mestranol, quinestranol, estradiol, estrone, estrin, estriol, estetrol, conjugated equine estrogens and precursors thereof, either alone or in combination with another estrogen and/or with another non-estrogen active. In some aspects, an estrogen delivered as part of the other active can be EE.

Incorporated progestogens can be any form of a progestogen or molecule capable of releasing such a progestogen in vivo or modulating the activity of a progestogen receptor. In aspects, at least one of the conception-regulating pharmaceutically acceptable ingredients comprises a progestogen receptor modulating compound. In aspects, such progestogens can be considered "progestogen receptor modulating means" where a means-plus-function description of the invention is desired. Such a progestogen can be any generation of progestogen(s) have a wide range of progestational (e.g. prevention of ovulation and reduction of menstrual bleeding) or androgenic (e.g. acne- or hair growth stimulation) activity. According to certain embodiments, one or more progestogens present in the other active dosage form can be a first-generation progestogen such as norethindrone, norethindrone acetate, and ethynodiol; second generation progestogen such as desogestrel and norgestrel; third generation progestogen such as norgestrel and norgestimate; or fourth generation progestogen such as dropspirenone. According to certain embodiments, any one or more progestogens present in the other active dosage form can be, but may not be limited to, levonorgestrel, norgestimate, norethisterone, dydrogesterone, drospirenone, 3-beta-hydroxydesogestrel, 3-keto desogestrel, etonogestrel, 17-deacetyl norgestimate, 19-norprogesterone, acetoxypregnenolone, allylestrenol, anagestone, chlormadinone, cyproterone, demegestone, desogestrel, dienogest, dihydrogesterone, dimethisterone, ethisterone, ethynodiol diacetate, flurogestone acetate, gastrinon, gestodene, gestrinone, hydroxymethylprogesterone, hydroxyprogesterone, lynestrenol, lynoestrenol, medrogestone, medroxyprogesterone, megestrol, melengestrol, nomegestrol, norethindrone, norethisterone, norethynodrel, norgestrel (includes d-norgestrel and dl-norgestrel), norgestrienone, normethisterone, progesterone, quingestanol, (17alpha)-17-hydroxy-11-methylene-19-norpregna-4,15-diene-20-yn-3-one, tibolone, trimegestone, algestone acetophenide, nestorone, promegestone, 17-hydroxyprogesterone esters, 19-nor-17hydroxyprogesterone, 17alpha-ethinyl-testosterone, 17alpha-ethinyl-19-nor-testosterone, d-17beta-acetoxy-13beta-ethyl-17alpha-ethinyl-gon-4-en-3-one oxime and precursors of these compounds. In some embodiments the progestogen used in the progestogenic phase is selected from the group consisting of levonorgestrel, norgestimate, norethisterone, drospirenone, dydrogesterone as well as precursors thereof, either alone or in combination with another progestogen and/or another non-progestogen active.

Steroids that are contained in the additional dosage form of an intermittent vitamin B12 compound dosing regimen method can be present either alone or in any combination with one another. According to certain embodiments, any one or more steroids contained in the additional dosage form of an intermittent vitamin B12 compound dosing regimen, e.g. one or more estrogens or progestogens alone or in combination, can also be considered means for controlling ovulation where a means-plus-function characterization of such aspects of the invention is desired.

According to some embodiments the subject, e.g. a menstruating woman or woman otherwise experiencing recurring vaginal discharge of blood, is receiving treatment with a steroid pharmaceutical agent before a treatment period during which the vitamin B12 compound dosage form is administered and/or the vitamin B12 compound dosage form is received. In some embodiments, the one or more additional dosage forms comprises a series of three forms forming a triphasic steroid contraceptive, hormone replacement therapy, or other steroid-hormone treatment regimen.

In some embodiments, the steroid pharmaceutical agent is in the form of a single steroid hormone. In alternative embodiments, the steroid pharmaceutical agent is in the form of a combination steroid hormone treatment. In one aspect the steroid pharmaceutical agent is a combination of two or more steroid hormones. In one aspect, the concentrations of one or more steroid hormones in the steroid pharmaceutical agent remain constant across each dose or set of doses in the vitamin B12 compound-free portion of the dosing regimen. For example, the non-treatment part of the cycle can comprise two, three, or more periods in which different second dosage forms are administered, such as different hormones or differing amounts of steroid hormones. In one aspect the concentration of one or more steroid hormones in a steroid pharmaceutical agent changes across such dosing periods.

In a further exemplary embodiment, the steroid pharmaceutical agents that are administered during the intervening period of a cyclic regimen method (in which no vitamin B12 compounds are administered to the subject), are provided in a regimen that is in the form of a multiphase steroid hormone treatment (each phase of each applicable cycle having a different dosage concentration, amount, frequency and/or form of one or more steroid hormones administered during the applicable phase). According to some aspects, any one or more steroid hormones administered to a patient as part of such a multiphase regimen can increase in concentration and/or amount across or within administered phases of treatment (e.g., the concentration of one or more hormones administered to a patient can increase from day-to-day within a single week or can increase from week-to-week in a multi-week cycle, e.g., a cycle of about 28 days). According to alternative aspects, any one or more steroid hormones can decrease in concentration and/or amount administered across or within a given period (e.g., within a week) across two, three, or more phases of a treatment cycle (e.g., within about a month, such as 28 days). In other aspects, the amount of steroid hormones administered to the patient in a period of a cycle can change two or more times (often two or three times) by increases and/or decreases in dosages/amounts of steroid hormone administered in the different phases of the treatment cycle (e.g., a method can comprise a decrease in amount administered in week two of the treatment cycle as compared to week one, followed by a further decrease in amount administered in week three as compared to week two; or in alternative embodiment, an increase in week two as compared to week one, but a decrease in week three as compared to week two and/or week one of the cycle).

In some aspects, the multiphase steroid hormone treatment is a triphasic contraceptive or hormone replacement therapy treatment. In some aspects, the triphasic contraceptive or hormone replacement therapy treatment can be any treatment wherein steroid hormones are administered in three differing formulations. According to one embodiment, the triphasic contraceptive comprises a first phase of a progestogen and an estrogen; a second phase of a progestogen and an estrogen wherein the amount of progestogen is higher than that of the first phase; and a third phase of a progestogen and an estrogen wherein the amount of progestogen is higher than that of the first or the second phase, and wherein the amount of estrogen remains constant throughout all three phases. Several examples of such triphasic contraceptive regimens are known in the art.

In one aspect, the steroid hormone treatment is a birth control method that is classifiable as a low dose birth control method (e.g., a method in which less than 50 mcg, less than 40 mcg, less than 35 mcg, less than 30 mcg, less than 25 mcg, or about 20 mcg or less of one or more estrogens is administered on steroid hormone treatment days in the birth control treatment regimen). In another aspect, the steroid hormone treatment is a progestin-only birth control treatment. Examples of such treatments are known in the art.

According to certain embodiments, a multiphasic steroid hormone treatment can be administered during the intervening period (in which no vitamin B12 compounds are administered to the subject) wherein the multiphasic steroid hormone treatment period last for approximately 21 days, such as for example between about 10 and about 30 days, or for example between about 15 and 25 days. In some aspects each phase of the multiphasic steroid hormone treatment can last approximately 7 days, such as for example each phase can last between about 1 day and about 15 days, such as for example between about 5 and about 10 days.

The concentration of any one or more steroid hormones in the pharmaceutical agent can be any pharmaceutically acceptable concentration suitable for treating the patient according to the aim of the treatment protocol, the treatment protocol being dependent on the condition being treated. Steroid hormones can be given in a wide range of amounts and/or concentrations as is well understood in the art. For example, in certain embodiments one or more steroids in an additional dosage form of an intermittent vitamin B12 compound dosing regimen can be present in an amount ranging from about 2 mcg to about 30 mg, such as for example between about 10 mcg and about 5 mg, such as for example between about 20 mcg and about 1 mg.

According to such and other embodiments, the amount of any single dose of the vitamin B12 compound dosage form of one of the inventive methods typically will be dictated taking into consideration the intended outcome and/or administration regimen to be applied using the vitamin B12 dosage form.

In one aspect, a total amount of vitamin B12 compound administered as part of a vitamin B12 compound dosage form regimen does not exceed approximately 150 mcg per month. Accordingly, in some embodiments wherein the vitamin B12 compound treatment period is a continuous period (e.g., a period lacking any therapeutically significant interruptions of the dosing regimen) the amount of vitamin B12 compound per dose often will be a relatively small amount, such as less than about 6 mcg per dose, such as for example approximately 1-5 mcg per dose, as in approximately 2-4 mcg, with any such dose typically being administered daily.

According to alternative embodiments wherein the vitamin B12 treatment period is intermittent (cyclic) or otherwise non-continuous, the amount per dose can be a similar amount to those described above, or, alternatively, a dose greater than about 5 mcg per dose. For example, in such an aspect the invention provides a dosing regimen comprising an approximately 7 day treatment period comprising about 7 consecutive days of vitamin B12 compound dosage form administration followed by an approximately 21-day period wherein no vitamin B12 compound dosage form is administered, each of which cycle can comprise administration of up to about 30 mcg/day, such as between about 1-25 mcg, as in approximately 1-20 mcg, such as about 1-10 mcg or about 1-5 mcg, such as for example between about 5-20 mcg or between about 10-25 mcg, which amount of vitamin B12 can be administered daily for the 7 day treatment period. Because of the cyclic nature of administration of the vitamin B12 dosage form the total amount of vitamin B12 administered in any such cycle will still be relatively very low as compared to current leading supplementation regimens (e.g., representing less than about 50%, less than about 40%, less than about 30%, or even less than about 20% of the amount of vitamin B12 delivered over a corresponding total period of time in such regimens. According to embodiments a maximum of about 200 mcg of vitamin B12 compound per total cycle, such as about 150 mcg per cycle or less, about 100 mcg per cycle or less, about 70 mcg per cycle or less, about 50 mcg per cycle or less, about 40 mcg per cycle or less, or even about 30 mcg per cycle or less is administered to the subject in the practice of such a cyclic or otherwise intermittent regimen.

In another exemplary aspect, in a cyclic treatment regimen comprising administering a vitamin B12 compound dosage form for a treatment period of about 3 days followed by approximately 25-27 days of no vitamin B12 compound dosage administration, each vitamin B12 compound dosage form that is administered during the treatment period of such a cycle can comprise about 60 mcg of vitamin B12 compound or less, such as between about 1-50 mcg, between about 2-40 mcg, between about 5-35 mcg, or, for example, between about 3-30 mcg, such as between about 5-50 mcg, or, for example, between about 7-35 mcg administered daily for the 3 day treatment period. It is also possible that either in a cyclic or continuous regimen the amount of vitamin B12 compound administered on any given day or sub-period(s) of the treatment period can vary (e.g., in a low to high to low regimen; a high to low regimen; or low to high regimen).

According to one aspect of the invention, the dosage forms (which, as noted previously, can also be described as dosage units), comprising vitamin B12 will be detectably free, substantially free, or essentially free of an estrogen and/or a progestogen. According to one embodiment, the vitamin B12 compound dosage units typically are similarly substantially free, essentially free, or free of any steroid drug or any pharmaceutically active amount of any steroid drug.

In one particular aspect, the vitamin B12 compound dosage form is administered in a cyclical fashion with a pharmaceutical agent comprising a steroid, the vitamin B12 compound dosage form being administered for a cycle during a part of the cycle wherein recurring vaginal bleeding is expected or likely and the steroid being administered during some, most, or all of the other part of the cycle. According to some aspects, the vitamin B12 dosage treatment period and the steroid treatment period do not overlap at all or by more than 1 or 2 days. According to some aspects, the vitamin B12 compound dosage treatment period is shorter than the steroid treatment period (e.g., the vitamin B12 compound treatment period is about ½ as long or less, about $4/10^{th}$ as long or less, or about $1/3^{rd}$ as long or less than the steroid treatment period). In some aspects, the vitamin B12 compound dosage treatment period is longer than the steroid treatment period.

According to certain embodiments, the period of administration of the vitamin B12 compound dosage form in such methods involving the administration of steroids, such as contraceptive steroid hormones, can be at least one day, for example at least about 1 day, at least about 2 consecutive days, such as at least about 3 consecutive days, at least about 4 consecutive days, at least about 5 consecutive days, at least about 6 consecutive days, at least about 7 consecutive days, at least about 8 consecutive days, at least about 9 consecutive days, at least about 10 consecutive days, or even more, such as at least about 12 consecutive days, at least about 14 consecutive days, at least about 16 consecutive days, or at least about 18 consecutive days, such as for example at least about 20 consecutive days, at least about 22 consecutive days, at least about 24 consecutive days, at least about 26 consecutive days, or at least about 28 consecutive days.

Whether performed in connection with the administration of a second agent (e.g. one or more additional actives) or not, in some embodiments the methods of the invention also or alternatively provide methods which provide at least 2 consecutive daily dosages of low dose vitamin B12 compound, such as for example between 1 mcg and 5 mcg of a vitamin B12 compound (e.g., about 1.5 mcg-3.5 mcg, e.g., between about 1.75-about 3.25 mcg, or between about 1.8 mcg and about 3 mcg) as will be described further elsewhere herein.

The phrase "continuous administration" when used in relation to the administration of one or more active principles, typically means that said one or more active principles (e.g., active pharmaceutical agents, nutritional supplements, or associated dosage forms) are administered at relatively regular intervals, with no (therapeutically) significant interruptions. Such methods can allow for minor interruptions (e.g., of 1 day, 2 days, 3 days, 5 days or less, or 7 days or less) that do not affect the overall effectiveness of the present methods, and indeed such deviations from "continuous administration" are typically encompassed by such methods (however, in other embodiments they are not). In one embodiment, an administration regimen is deemed to be continuous if the longest interval between 2 subsequent administrations is not more than 4 times as long as the average interval of administration (e.g., no more than 3 days in a daily administration regimen). "Continuous administration" herein usually is used to described methods in which a composition, such as a vitamin B12 dosage form, is administered to the subject on a regular basis (e.g., once a day) without significant intervening non-treatment periods (in this respect the term is often used to describe methods other than intermittent regimens). However, the term also can be used to describe periods of regular administration during a longer relevant period, such as a treatment period of a cycle in which vitamin B12 compounds are administered every day. The meaning of the term is expected to be clear to the reader given the context of such use.

According to some embodiments, the dosage form of a vitamin B12 compound, e.g. unit doses of the vitamin B12 compound dosage form, are provided for an approximate one week period, for example about a 3 day treatment period, about a 4 day treatment period, about a 5 day treatment period, about a 6 day treatment period, about a 7 day treatment period, about an 8 day treatment period, about a 9 day treatment period, or about a 10 day treatment period following an approximate 3 week multiphasic administration of one or more compositions comprising an estrogen and a progestogen, such as for example about a 14 day treatment period, about a 16 day treatment period, about an 18 day treatment period, about a 20 day treatment period, about a 22 day treatment period, about a 24 day treatment period, about a 26 day treatment period, or about a 28 day treatment period comprising administration of an estrogen and a progestogen. According to some aspects, the vitamin B12 dosage form is provided for approximately 7 days followed by a treatment period comprising a triphasic administration of one or more compositions comprising an estrogen and a progestogen for approximately 21 days.

According to certain aspects, the vitamin B12 dosage form of the invention is administered to a recipient in an amount less than 5 mcg per day, often for a limited time period, on a cycling schedule, as described above. In some aspects the administration of the vitamin B12 composition is associated with a physiological condition, which may be a recurring physiological condition or physiological challenge. In some aspects, the recurring physiological challenge is the monthly bleeding cycle of a human female. According to certain aspects, the vitamin B12 compound dosage form is administered to a human female on a cycling schedule corresponding with an expected period of recurring physiological challenge such as the woman's monthly bleeding cycle, and wherein the vitamin B12 compound dosage form comprises a methylcobalamin compound, such as a form of a naturally sourced methylcobalamin or a form of a bioidentical methylcobalamin (e.g., a suitable salt thereof).

According to certain embodiments, the vitamin B12 compound dosage form comprises the vitamin B12 compound component in an amount that is substantially lower than the typical amount of supplement dosage forms on the market, such as a single dose not exceeding 5 mcg, such as for example a single dose of the vitamin B12 compound comprising no more than about 5 mcg, no more than about 4.5 mcg, no more than about 4 mcg, no more than about 3.5 mcg, no more than about 3 mcg, no more than about 2.5 mcg, no more than about 2 mcg, no more than about 1.5 mcg, or no more than about 1 mcg. According to certain aspects, a single dose of a vitamin B12 compound dosage form composition of the invention, or alternatively stated a single unit of a vitamin B12 compound dosage form composition can comprise between 1-5 mcg of a vitamin B12 compound, about 1.5-4.5 mcg of a vitamin B12 compound, or for example between about 2-3 mcg of a vitamin B12 compound. In some embodiments a single dose comprises about 2.5 mcg of a vitamin B12 compound (e.g., about 2.3 or 2.4 mcg of a methylcobalamin compound). In certain aspects, the vitamin B12 compound is a methylcobalamin compound, such as a natural or bioidentical form of methylcobalamin.

In some aspects, the total amount of a vitamin B12 compound administered in a single dosing period of a treatment cycle does not exceed 30 mcg. For example in one embodiment, the total amount of a vitamin B12 compound administered in a single treatment period encompassed within in a period of one month (e.g. approximately 4 weeks, e.g. 28 days) is no more than about 30 mcg, no more than about 28 mcg, no more than about 26 mcg, no more than about 24 mcg, no more than about 22 mcg, no more than about 20 mcg, or no more than about 20 mcg, such as no more than about 18 mcg of a vitamin B12 compound is administered as part of the vitamin B12 dosage form during any approximately 1 month (e.g., 28 day) period. According to certain embodiments, a total dosing regimen can comprise a total amount of a vitamin B12 compound administered over the course of an approximately 1 month period during a defined vitamin B12 treatment period of consecutive days is less than 18 mcg, such as less than about 18 mcg, less than about 17.8 mcg, less than about 17.6 mcg, less than about 17.4 mcg, or even less than about 17.2 mcg, such as less than about 17 mcg, less than about 16.8 mcg, less than about 16.6 mcg, less than about 16.4 mcg, less than about 16.2 mcg, or less than about 16 mcg. In some embodiments, the total amount of a vitamin B12 compound administered as part of the vitamin B12 compound dosage form during any treatment period encompassed by a one month total dosing cycle can be between 16-30 mcg, such as between about 16.2 and about 25 mcg, between about 16.4 and about 20 mcg, between about 16.6 and about 18 mcg, or between about 16.7 and 17 mcg. In certain embodiments the total amount of a vitamin B12 compound administered during a single treatment period is between 16 and 17 mcg, for example about 16.8 mcg. In some aspects, the vitamin B12 compound in the vitamin B12 compound dosage form is a form of methylcobalamin, e.g., a salt thereof.

Vitamin B12 compositions can be administered to female subjects by any suitable route of administration. Typically, administration will be via oral administration of a suitable oral administration dosage form, examples of which are further described elsewhere herein. In other aspects, a vitamin B12 compound dosage form can be administered via injection, infusion, inhalation, absorption or by any method in combination with other known techniques. "Administering" in this respect can include the act of self-administration or administration by another person such as by a health care provider. In one aspect, administering is performed subject to the direction of a physician or other learned intermediate with medical training, although such administration can still be performed as self-administration.

Subjects and Outcomes

According to certain embodiments, the vitamin B12 compound dosage form treatment regimens of the invention can be administered to any mammalian subject. In other aspects, the mammalian subject is a human subject. In some embodiments, as noted elsewhere herein, the human subject is a female. In certain aspects, the human female subject is a female experiencing a recurring bleeding cycle due to menstruation or breakthrough bleeding.

In some embodiments a female experiencing a recurring vaginal discharge of blood shows no signs or symptoms of a vitamin B12 deficiency. In some aspects, the female experiencing a recurring vaginal discharge of blood shows one or more signs or symptoms of being vitamin B12 deficient, such as for example weakness, fatigue, lightheadedness, heart palpitations, shortness of breath, pallor, a smooth tongue, constipation, diarrhea, loss of appetite, gaseousness, neuropathic symptoms such as numbness or tingling, muscle weakness, difficulty walking, vision impairment or loss, or a change in mental state such as depression, memory loss, behavioral symptoms and the like, or changes in physiological, biological or biochemical markers specific to or impacted by vitamin B12. In some embodiments the female experiencing a recurring vaginal discharge of blood is identified as belonging to a group at risk for suffering from a condition associated with vitamin B12 deficiency such as older adults, individuals with pernicious anemia, individuals with gastrointestinal disorders such as celiac disease and Crohn's disease, individuals having had gastrointestinal surgery, those subject to certain hormone treatments, or those on certain restricted diets, such as those low in or devoid of animal-sourced foods. In one aspect the subject consumes a vegetarian or vegan diet. In one aspect, the subject also or alternatively is subject to a steroid drug dosing regimen, such as a birth control or hormone replacement therapy regimen comprising an estrogen. According to other aspects, the individuals treated by the practice of the method are also or alternatively diagnosed with, are at significant risk for developing, have experienced, or exhibit signs or symptoms of pernicious anemia, a gastrointestinal disorder (such as Crohn's disease or Celiac disease), or a recent gastrointestinal surgery. In one aspect, the subject also or alternatively is a subject that may be physiologically challenged by mild or moderate blood loss, which may be blood loss associated with menstruation or breakthrough bleeding. The methods for the diagnosis of such conditions are known in the art (e.g., vitamin B12 deficiency is described in, for example, Allen et al. (1990) Am. J. Hematol. 34: 90-98; Lindenbaum et al. (1990) Am. J. Hematol. 34: 99-107; Lindenbaum et al. (1988) N. Engl. J. Med. 318: 1720-1728; Beck (1991) in Neuropsychiatric Consequences of Cobalamin Deficiency, Mosby Year Book 36: 33-56; Moelby et al. J Intern Med (1990) 228: 373-378; and Ueland and Refsum (1989) J. Lab. Clin. Med. 114: 473-501; Pennypacker et al. J Am Geriatr Soc (1992) 40: 1197-1204). In one facet of the invention, a treatment regimen provided herein is administered to a female that also or alternatively exhibiting any one or more sign(s) of such condition(s), e.g., elevated serum levels of homocysteine, cystathionine, methylmalonic acid and/or 2-methylcitric acid.

According to certain aspects of the invention, the vitamin B12 dosage form and the associated method of administration is suitable for administration to pregnant human female subjects. According to alternative embodiments of the invention, the vitamin B12 dosage form and any associated method of administration should not be administered to pregnant human female subjects and such subjects are excluded from the target patient population.

Females of childbearing ability, experiencing a menstrual cycle or monthly breakthrough bleeding (e.g. are experiencing a recurring vaginal discharge of blood) are prone to low red blood cell counts, specifically during the time periods every month (e.g. approximately every 24-32 days) when recurring vaginal bleeding occurs. Such blood loss may mean that enhanced replenishment of blood (in amount or time) is desirable, which may be promoted by administration of vitamin B12 compounds according to the regimens described here.

According to certain embodiments, those benefiting from the vitamin B12 dosage forms of the invention include human female subjects between the ages of about 10 to about 70 years of age, such as those between about 12 and about 65 years of age, as in for example women between the ages of about 14 to about 60 year of age, such as for example women between the ages of about 15 and about 55 years of age. According to certain embodiments, the target population for the vitamin B12 compound dosages of the invention is a population of women having an average age of approximately 35 years or older, such as an average age of about 35 years, about 36 years, about 37 years, about 38 years, about 39 years, about 40 years, or for example an average age of about 41 years, about 42 years, about 43 years, about 44 years, about 45 years, or about 46 years, such as for example having an average age of approximately 47 years, approximately 48 years, approximately 49 years, or for example a population of human females having an average age of approximately 50 years. In some aspects, the subject also or alternatively is a woman of between about 35 years of age and 70 years of age, such as for example those between about 35 and about 70 years of age, between about 37 and about 68 years or age, or for example women between about 40 and about 65 years of age or about 40-60 years of age or about 35-60 years of age. Such women can be actively engaged in a hormone-based method of contraception administered in connection with the administration of the vitamin B12 compound, as exemplified elsewhere herein.

In some aspects, the method is performed in females with an active reproductive cycle. According to certain embodiments, the recipient population experiences either a consistent menstrual cycle; an inconsistent menstrual cycle; a consistent monthly reproductive cycle aided by hormone replacement therapy, hormone contraceptive birth control method, or other contraceptive; or an inconsistent monthly reproductive cycle (i.e., an inconsistent recurring monthly hormonal cycle or other cycle including both a period of recurring vaginal discharge of blood, such as a period, and any intervening time between the next cycle of vaginal discharge bleeding) aided by hormone replacement therapy, a hormone contraceptive birth control method, or other contraceptive.

In some aspects of the invention, the subject administered the vitamin B12 compound dosage form of the invention can also be subject to a self-prescribed or health care provider-prescribed supplement regimen or otherwise often, situationally, or regularly consume one or more nutritional supplements (e.g., vitamins, minerals, or other supplements). In some embodiments, such supplements can be any general health supplement such as a vitamin, mineral, herbal compound or any derivative or combination thereof. In some embodiments the vitamin B12 compound dosage form is free of such ingredients itself but any one or more of such ingredients can be being used by the subject. In some embodiments, such ingredients can be folic acid and or iron. According to some aspects the vitamin B12 compound dosage forms of the invention do not comprise folic acid, do not comprise iron, or do not comprise either folic acid or iron, however the subject is using folic acid and/or iron nutritional supplementation in addition to the vitamin B12 oral dosage form of the invention.

In certain aspects, the vitamin B12 oral dosage form is administered in to a human female as a component of a hormone-comprising birth control method, and the presence of the vitamin B12 oral dosage form as part of the treatment regimen detectably or significantly increases, patient compliance with, or satisfaction with, the birth control method, as, e.g., measured by an appropriately powered and administered study (e.g., a clinician-conducted survey of users) over that of users receiving the birth control treatment alone. In aspects, users receiving a hormone-comprising birth control method comprising intermittent dosing of a vitamin B12 compound demonstrate at least a 0.5%, at least a 1%, at least a 3%, at least a 5%, at least a 10%, at least a 15%, or at least a 20% increase or more in compliance with a prescribed birth control method comprising a vitamin B12 compound over those receiving the same hormone-comprising birth control method without the intermittent dosing of a vitamin B12 compound as described herein.

Dosage Forms

Commonly the regimens disclosed here are provided by administering a vitamin B12 dosage form comprising a physiological relevant amount of a vitamin B12 compound in a pharmaceutically acceptable form. In one aspect, the vitamin B12 dosage form is an oral dosage form. In a more particular aspect, the vitamin B12 oral dosage form comprises a vitamin B12 compound as the sole active supplement or agent. According to alternative embodiments, the vitamin B12 oral dosage form comprises one or more additional actives or supplements.

According to some embodiments, the vitamin B12 compound dosage form of the invention does not comprise a source of gluten (i.e., can be classified as "gluten free"). In some embodiments, the dosage form is also or alternatively capable of being classified as "sugar free" under prevailing dietary standards. According to certain embodiments, the vitamin B12 compound dosage form does not comprise any element sourced from an animal or animal product and is therefore suitable for those following a restricted vegetarian or vegan diet.

The vitamin B12 compound dosage forms described herein can be provided in any suitable dosage form capable of being administered to a human subject. Often the dosage forms will be administered orally and are, accordingly, suitable for oral administration. In some embodiments, the oral delivery form can be in the form of a solid, for example the composition can be encapsulated within a hard or soft gelatin capsule, or provided as a tablet, pill, lozenge, dry granules, microgranules, or other solid oral dosage form suitable for swallowing or dissolution within the oral cavity. According to alternative embodiments, the oral delivery form can be in the form of a liquid, such as for example in a pre-mixed liquid or provided as a lyophilized powder to be reconstituted before use and administered as a liquid dosage form. According to certain embodiments, an oral delivery form can incorporate taste-masking compositions, e.g., a taste-masked tablet, taste-masked granules, taste-masked microgranules, or any combination thereof. In other embodiments, the pharmaceutical compositions of the invention are in the form of a plurality of granules, a plurality of microgranules, a plurality of taste-masked granules, a plurality of taste-masked microgranules, or a combination thereof.

In some embodiments, the vitamin B12 compound compositions of the invention are in the form of a vaginal suppository, an injection, a subdermal delivery system, a gel, cream, or other transdermal delivery system such as a transdermal patch, or any other suitable delivery system capable of delivering a vitamin B12 compound in a form capable of aiding in the relief of one or more vitamin B12 deficiency symptoms and/or being available for contribution to healthy hematopoiesis.

According to certain embodiments, the dosage forms described herein are tablets. In some aspects the tablets are for oral consumption.

In some aspects the total amount of a vitamin B12 compound in each tablet dosage form administered to the subject, is less than about 0.01 wt. % of the tablet or other applicable dosage form, such as less than about 0.009 wt. %, less than about 0.008 wt. %, less than about 0.007 wt. %, less than about 0.006 wt. %, less than about 0.005 wt. %, less than about 0.004 wt. %, or even less than about 0.003 wt. % of the dosage form/tablet. In some aspects, the tablet comprises an amount of a vitamin B12 compound that ranges between 0.001-0.003 wt. % of the tablet, such as about 0.002-0.003 wt. % of the dosage form/tablet.

The remainder of the weight of the oral dosage unit, e.g. a tablet, can comprise an amount of one or more acceptable carriers/fillers or excipients. An "excipient" as used herein is a non-pharmaceutically active ingredient and/or a non-nutritional ingredient that imparts a detectable functionality to the dosage form, such as stability, anti-bacterial properties, disintegration, compressibility, etc. Numerous excipients are known in the art. Also or alternatively the dosage form can include non-functional ingredients, which may be classified interchangeably as carriers or diluents.

Dosage forms can generally include any suitable carrier, suitable excipient, or combination thereof. Numerous examples of such ingredients which can be classified as, e.g., fillers, binders, (e.g., hydroxypropyl methylcellulose, polyvinylpyrrolidone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc) are known in the art. As such, these ingredients can be described as "carrier means" or "means" for carrying out their respective functions (e.g., disintegrating means), in descriptions of the invention using means-plus-function terminology.

In certain embodiments, the dosage forms used in the methods of the invention include at least one pharmaceutically acceptable carrier or pharmaceutically acceptable excipient. The pharmaceutically acceptable excipient can be any suitable excipient such as but not limited to an inert core, one or more dispersion agents, one or more binding agents, one or more coating agents, one or more modified release coating agents, one or more stabilizing agents, one or more compression aids, one or more disintegrants, one or more anti-caking agents, one or more flow agents, one or more fillers, one or more colorants, or other similar or equivalent ingredients alone or in any combination thereof. In some embodiments, one or more components can perform multiple functions; for example, according to some embodiments, a binder, a compression aid, a texturizer, an anti-caking agent, and/or a coating agent can be means for providing stabilization of the dosage form and can therefore be considered stabilizing means in addition to their functions as a binder, compression aid, texturizer, anti-caking agent, coating agent, or other such function.

In some aspects, an excipient can be one or more of a saccharide, such as a monosaccharide, disaccharide, or other polysaccharide, a fatty acid such as a long or short chain fatty acid, a phosphate, a polymer, a plasticizer, a pigment, or any combination thereof. According to some aspects, an excipient can be a dicalcium phosphate, lactose monohydrate, microcrystalline cellulose, croscarmellose sodium, magnesium stearate, or any combination of the same.

In some aspects a coating material can be incorporated in a dosage form formulation. A coating agent can be any pharmaceutically acceptable coating agent capable of protecting the tablet contents and/or facilitating ease of swallowing. In some aspects the coating agent is an aqueous film. An exemplary aqueous film coating agent is an Opadry® coating agent (Colorcon Inc., global headquarters in Harleysville, Pa., USA). In some aspects the coating agent can also provide a colorant. The colorant can be any color selected to provide a chosen visual characteristic to the tablet. In some aspects, the colorant is green Opadry® or yellow Opadry®. In a particular aspect of the invention, the coating agent is yellow Opadry®. The colorant can be used to separately identify the vitamin B12 compound dosage form from other secondary dosage forms in methods and compositions involving a combinations of such dosage forms, such as those combining a triphasic birth control method with a vitamin B12 compound supplementation method of the invention.

Unlike many pharmaceutical tablets and/or supplement tablets, the vitamin B12 compound dosage form tablets of certain embodiments typically are of relatively small size, which may promote compliance and reduce unpleasant experiences associated with administration (e.g., by promoting ease of swallowing). According to certain embodiments, the weight of each of the tablets or other oral dosage form of the invention is less than about 200 mg, such as less than about 190 mg, less than about 180 mg, less than about 170 mg, less than about 160 mg, or less than about 150 mg. According to certain embodiments, the weight of the tablet or other oral dosage form is between about 10-200 mg, such as between about 20-180 mg, such as between about 30-170 mg, for example between approximately 40-160 mg, or between about 50-150 mg.

In an exemplary embodiment, the oral dosage form comprises a vitamin B12 compound in the form of a methylcobalamin compound. In some aspects the methylcobalamin compound is present in the dosage form in about 1-3 mcg, such as for example between about 1.5-2.5 mcg, such as about 2-2.5 mcg.

According to some embodiments, the vitamin B12 compound dosage form comprises one or more flow agents. In certain aspects the vitamin B12 compound dosage form can comprise any pharmaceutically acceptable flow agent capable of providing suitable characteristics for manufacturing purposes. Exemplary flow agents suitable for the vitamin B12 compound dosage forms of the invention include but are not limited to minerals such as talc or silica, fats such as vegetable stearin, stearic acid and/or its salts (e.g. magnesium stearate), dicalcium phosphate and the like. In some aspects, the flow agent is dicalcium phosphate. According to certain embodiments, the vitamin B12 compound dosage form of the invention comprises between about 0.1-0.4 mg of dicalcium phosphate, such as between about 0.15-0.35 mcg, as in between about 0.2-0.3 mcg, such as between about 0.22-0.25 mcg dicalcium phosphate. According to certain aspects, the dicalcium phosphate is present in an amount which does not exceed 0.5 wt. % of the tablet. In some aspects, the dicalcium phosphate represents between about 0.1-0.5 wt. % of the tablet. For example, in some aspects the tablet comprises between about 0.1-0.4 wt. % dicalcium phosphate, such as between about 0.1-0.3 wt. % dicalcium phosphate, as in for example between about 0.15-0.25 wt. %, or for example approximately 0.2 wt. % dicalcium phosphate.

According to certain aspects, the vitamin B12 compound dosage form of the invention comprises magnesium stearate. In some aspects, the vitamin B12 dosage form of the invention comprises between about 0.1-0.8 mg magnesium stearate, as in between about 0.2-0.7 mg, such as between about 0.3-0.6 mg, or between about 0.4-0.6 mg magnesium stearate. According to certain aspects, the magnesium stearate is present in an amount which does not exceed 1 wt. % of the tablet. In some aspects, the magnesium stearate represents between 0.1-0.9 wt. % of the tablet. For example, in some aspects the tablet comprises between about 0.1-0.9 wt. % magnesium stearate, between about 0.2-0.8 wt. % magnesium stearate, between about 0.4-0.6 wt. % magnesium stearate, or for example between about 0.45 and 0.55 wt. % magnesium stearate. According to some aspects, the vitamin B12 compound dosage form comprises approximately 0.5% magnesium stearate.

In certain embodiments, the vitamin B12 compound dosage form comprises one or more compression aids. In certain aspects the vitamin B12 compound dosage form can comprise any pharmaceutically acceptable compression aid capable of providing suitable characteristics for manufacturing purposes. Exemplary compression aids suitable for the vitamin B12 compound dosage forms of the invention include but are not limited to a synthetic polymer, starch, sugar, sugar alcohol, cellulose or a derivative of a cellulose, and the like. In some aspects, the compression aid is lactose monohydrate. According to certain embodiments, the vitamin B12 compound dosage form of the invention comprises between about 60 and 75 mg of lactose monohydrate, such as for example between about 62-70 mg lactose monohydrate, as in for example between about 64-68 mg, such as between about 65 and 67 mg of lactose monohydrate. According to certain aspects, the lactose monohydrate is present in an amount which does not exceed 75 wt. % of the tablet. In some aspects, the lactose monohydrate represents between about 60-75 wt. % of the tablet. For example, in some aspects the tablet comprises between about 62-70 wt. % lactose monohydrate, between about 64-68 wt. % lactose monohydrate, or for example between about 65-67 wt. % lactose monohydrate. In some aspects, the vitamin B12 compound dosage form comprises about 67 wt. % lactose monohydrate.

In one aspect, the vitamin B12 compound dosage form comprises one or more texturizers or anti-caking agents. In certain aspects, the vitamin B12 compound dosage form can comprise any pharmaceutically acceptable texturizer or anti-caking agent capable of providing suitable characteristics for manufacturing purposes. Exemplary texturizers or anti-caking agents suitable for the vitamin B12 compound dosage forms of the invention include but are not limited to a silicate, e.g. calcium silicate or sodium aluminosilicate, stearates of calcium and magnesium, talc, flour, starch and the like. In some aspects, the texturizer or anti-caking agent is microcrystalline cellulose. Microcrystalline cellulose can also contribute to compressibility of some formulations. According to some aspects, the vitamin B12 compound dosage form of the invention comprises between about 15-25 mg microcrystalline cellulose, such as between about 17-25 mg, such as between about 19-24 mg, as in between about 20-22 mg microcrystalline cellulose. According to certain aspects, the microcrystalline cellulose is present in an amount which does not exceed 25 wt. % of the tablet. In some aspects, microcrystalline cellulose represents approximately 15-25 wt. % of the tablet. For example, in some aspects the tablet comprises between about 17-23 wt. % microcrystalline cellulose, such as between about 19-21 wt. % microcrystalline cellulose, as in between about 20-21 wt. % microcrystalline cellulose. According to some aspects, the vitamin B12 compound dosage form of the invention comprises about 21 wt. % microcrystalline cellulose.

In some aspects, the vitamin B12 compound dosage form comprises a means for disintegrating an oral dosage form such as a tablet upon or following ingesting. In one embodiment, the vitamin B12 compound dosage form comprises one or more disintegrants. In certain embodiments, the vitamin B12 compound dosage form can comprise any pharmaceutically acceptable disintegrant capable of providing suitable breakdown, disintegration, or dissolution characteristics of the final dosage form after or upon ingestion. Exemplary disintegrants suitable for the vitamin B12 compound dosage forms of the invention include but are not limited to compounds which swell or dissolve in water, for example a starch, cellulose derivative, and alginates; crosslinked polymers, e.g. crospovidone, crosslinked sodium carboxymethylcellulose (croscarmellose sodium), and the like. In some aspects, the disintegrant is croscarmellose sodium. According to some aspects, the vitamin B12 compound dosage form of the invention comprises between about 5-15 mg of croscarmellose sodium, such as between about 7-13 mg, as in between about 9-11 mg of croscarmellose sodium. According to certain aspects, the croscarmellose sodium is present in an amount which does not exceed 15 wt. % of the tablet. In some aspects, croscarmellose sodium represents between about 5-15 wt. % of the tablet. For example, in some aspects the tablet comprises between about 7-13 wt. % croscarmellose sodium, such as between about 9-11 wt. % croscarmellose sodium, as in between about 9.5-10.5 wt. % croscarmellose sodium. According to certain aspects, the vitamin B12 compound dosage form of the invention comprises about 10 wt. % croscarmellose sodium.

According to certain embodiments, the vitamin B12 compound dosage form comprises one or more coating agents. In some aspects, the vitamin B12 compound dosage form can comprise any pharmaceutically acceptable coating agent capable of providing suitable protective and administrative characteristics of the final dosage form. Exemplary coating agents suitable for the vitamin B12 compound dosage forms of the invention include but are not limited to sugars, natural or synthetic polymers, plasticizers, gelatins, and the like. In some embodiments, the coating agent is Opadry® comprising polymer, plasticizer, and optionally a pigment. According to certain aspects, the vitamin B12 compound dosage form of the invention comprises between about 1 mg and about 4 mg of a coating agent, such as between about 1.5-3.5 mg, as in for example between about 2-3 mg of a coating agent. In some aspects, the coating agent comprises a colorant. The colorant can comprise any pharmaceutically acceptable colorant including but not limited to synthetic dyes and natural colors, naturally pigmented compounds, and the like. In some aspects the colorant is a green pigment. In alternative aspects, the colorant is a yellow pigment. In some aspects, the colorant is an incorporated element of the coating composition. According to certain embodiments, the colorant-coating combination is green Opadry®. In certain embodiments, the colorant-coating combination is yellow Opadry®. According to certain aspects, the green or yellow Opadry® is present in an amount which does not exceed 5 wt. % of the tablet. In some aspects, green or yellow Opadry® represents between about 1-5 wt. % of the tablet. For example, in some aspects the tablet comprises between about 1-4 wt. % green Opadry®, as in between about 1-3 wt. % green Opadry®, such as for example between about 1.5-2.5 wt. % green Opadry®. In certain embodiments, the vitamin B12 compound dosage form of the invention comprises about 2 wt. % green Opadry®. In an alternative example, in some aspects the tablet comprises between about 1-4 wt. % yellow Opadry®, as in between about 1-3 wt. % yellow Opadry®, such as for example between about 1.5-2.5 wt. % yellow Opadry®. In certain embodiments, the vitamin B12 compound dosage form of the invention comprises about 2 wt. % yellow Opadry®.

According to certain embodiments, the vitamin B12 compound dosage form is stable at about room temperature, e.g. at about 25 degrees Celsius, for example about 15-35 degrees Celsius, or for example between about 20-30 degrees Celsius, for at least about 12 months or more, for example for at least about 12 months, at least about 14 months, at least about 16 months, at least about 18 months, at least about 20 months, at least about 22 months, at least about 24 months or even more, for example at least about 26 months, at least about 28 months, at least about 30 months, at least about 32 months, at least about 34 months, or for example at least about 36 months. According to some embodiments, the vitamin B12 compound dosage form is stored protected from moisture, protected from light, protected from extreme changes in temperature, or any or all such conditions in combination.

Packaged Compositions

Vitamin B12 compound dosage forms and other vitamin B12 compound compositions, can be provided in any suitable packaging capable of maintaining stability of the compositions and facilitating ease of storage, ease of dispensation, ease of administration, ease of tracking administration, or any one or more of such characteristics. Such a package can be configured for regular re-use during the period in which the vitamin B12 composition is to be administered. In this respect, the package may be a pharmaceutically acceptable container-closure product container, such as are known in the art.

According to certain embodiments, the dosage form can be in a package comprising a plurality of dosage units. In some aspects, the dosage form is in tablet form packaged in a bottle or strip such as a blister strip or pack. In some embodiments, the dosage form can be arranged so as to indicate and facilitate sequential administration of the vitamin B12 compound dosage form and one or more additional dosage forms that do not comprise the vitamin B12 compound or that at least comprise one or more additional supplements or actives. In some aspects the dosage form can be arranged and adapted so as to facilitate successive daily administration of such dosage forms over two, three, four, or more periods, e.g., periods of a cycle. In some embodiments the dosage forms are tablets, capsules, or other solid dosage forms. In other embodiments, the oral dosage form can be in liquid form packaged in a bottle designed for administering a dose via pouring into a dosing cup or administration through a dropper.

According to certain embodiments, the vitamin B12 compound dosage forms of the invention are packaged such that more than one dose, e.g. more than one vitamin B12 compound dosage unit, is provided in the packaging. In some aspects, the more than one dose is provided in a capped container such as a bottle. In such aspects, the multiple doses are combined and are stored with one another in one storage space, not separated from one another. In some embodiments, the packaging for the vitamin B12 compound dosage forms of the invention is a container which lacks a specific indicator related to dosing schedule. For example, in some aspects the multiple doses can be provided in a tablet or pill bottle similar to that used for a common tablet or pill pharmaceutical prescription or, for example, an over the counter acetaminophen or other general over the counter medication in tablet, capsule, or similar orally administered form.

According to alternative embodiments, the vitamin B12 compound dosage forms of the invention can be package such that more than one dose is provided, and the packaging provides one or more specific indicators related to a dosing and/or administration schedule. For example, in some aspects the more than one dose is provided in a pack, e.g. a blister pack, wherein each individual dose or dosage unit is separated from every other individual dose or dosage unit. In some aspects, he unit dosages of the vitamin B12 compound composition and any other units of products provided therewith in the package (such as the various units of a triphasic birth control regimen to be administered in association with the vitamin B12 compound dosage forms), are organized according to class of such dosage forms, thereby aiding ease of recognition and appropriate use by the user. In some aspects, the packaging providing doses separated from one another allows the user to know, e.g. aids in communicating to a user, whether or not a dose has been administered (or e.g. consumed or "taken") on any particular day. According to some embodiments, the packaging can comprise one or more indicators which communicate to the user information about the dosing schedule, such as a date, a day of the week, one or more numbers in or of a dosing sequence, or the like. According to certain embodiments, the vitamin B12 compound dosage forms of the invention are packaged in a pack such as a blister pack, for example such a pack as may be provided for common cold medications wherein care in the amount of medication dispensed is particularly important, or for example the types of packs used for administration of orally administered contraceptive regimens (e.g. a monthly birth control pill regimen). In some aspects, the use of such packaging, e.g. a blister pack, allows for each individual dose of vitamin B12 compound-containing dosage form to be dispensed independently, without compromising the protective packaging of any other one or more doses.

According to certain embodiments, the packaging can comprise any number of doses of vitamin B12 compound dosage forms. According to common embodiments, the packaging can comprise between about 1 and about 30 doses of a vitamin B12 compound, such as for example between about 1 and about 28 doses, such as for example between about 1 and about 20 doses, between about 2 and 10 doses, or for example between about 3 and 7 doses. In some aspects the individual doses are separated from one another such that the administration of one does not compromise the sealed packaging of any one or more other doses. In some aspects the doses are arranged within the packaging so as to indicate sequential dosing according to a schedule, such as the doses may be arranged in a line or grouped together so as to indicate that each dose is to be taken as part of a sequence of doses.

The vitamin B12 compound dosage forms of the invention can be packaged in packaging devoid of any other dosage form. That is, in some aspects the vitamin B12 compound dosage forms of the invention are provided as the sole dosage form in a package. According to alternative embodiments, the vitamin B12 compound dosage forms of the invention can be provided in packaging containing one or more other dosage forms, such as, for example, one or more other dosage forms containing one or more other actives. According to certain embodiments, the one or more other dosage forms can comprise a placebo (e.g. a dosage form devoid of any active ingredient), one or more other vitamins, minerals, general health supplements, or one or more active pharmaceutical ingredients such as a drug. In some aspects such a drug can be any drug to be administered as part of a treatment regimen inclusive of the vitamin B12 compound dosage form. According to one embodiment, the one or more other dosage forms can comprise one or more steroid hormones. In one particular aspect, the vitamin B12 compound dosage forms of the invention are packaged with a multiphasic hormone treatment regimen. In some aspects, the multiphasic hormone treatment regimen is a triphasic birth control method. In some aspects, the packaging provides one or more indicators to the user of the sequence to be followed for administration, such as for example, which provided dosage form is to be taken which day and in what sequence the provided dosage forms should be consumed. In some aspects, each dose of the vitamin B12 compound-containing dosage form and each dose of any accompanying dosage form is stored within the packaging separately from any other dose such that the administration of any one single dose does not compromise the sealed packaging of any other single dose, such as can be accomplished using blister packs.

EXEMPLARY EMBODIMENTS & APPLICATIONS OF THE INVENTION

The following description of exemplary embodiments and features of the invention and the characterization or application thereof further illustrate various aspects of the invention but should not be construed in any way as limiting the scope of the claims or the rest of the disclosure provided herein.

Example 1

This example provides an illustrative composition of a vitamin B12 compound dosage form according to certain aspects of the invention and that also is suitable for application of several of the inventive methods described herein.

One exemplary composition of the vitamin B12 compound dosage form is manufactured according to the following formulation:

TABLE 1

| Vitamin B12 Tablet Exemplary Formulation 1 | |
|---|---|
| INGREDIENT | AMOUNT (mg) |
| Methylcobalamin 1% with Dicalcium Phosphate* | 0.24 |
| Lactose Monohydrate | 66.569 |
| Microcrystalline Cellulose | 20.65 |
| Croscarmellose Sodium | 9.742 |
| Magnesium Stearate | 0.487 |
| Green Opadry | 2.192 |

Exemplary Formulation 1 is compressed into approximately 100 mg tablets and loaded into a blister pack comprising 7 individual doses of 2.4 mcg methylcobalamin.

The dosage form can be provided along with instructions for a user to take one tablet per day for 7 days during a recurring cycle of 28 days for vitamin B12 supplementation, wherein the 7 day vitamin B12 treatment period can be selected to coincide with a period of expected recurring vaginal bleeding.

Example 2

This Example provides an alternative illustrative composition of a vitamin B12 compound dosage form that also is suitable for application in several of the inventive methods described herein.

The formulation of the vitamin B12 compound dosage form is manufactured according to the following formulation:

TABLE 2

| Vitamin B12 Tablet Exemplary Formulation 2 | |
|---|---|
| INGREDIENT | AMOUNT (mg) |
| Methylcobalamin 1% with Dicalcium Phosphate* | 0.24 |
| Lactose Monohydrate | 66.569 |
| Microcrystalline Cellulose | 20.65 |
| Croscarmellose Sodium | 9.742 |
| Magnesium Stearate | 0.487 |
| Green Opadry | 2.192 |

Formulation 2 is compressed into approximately 100 mg tablets and loaded into a blister pack comprising 7 individual doses of 2.4 mcg methylcobalamin. The blister pack also contains 21 other active dosage forms. The 21 other active dosage forms are comprised of 3 separate formulations, each provided as a set of 7 tablets. The other active dosage forms are in the form of a triphasic hormone treatment containing the following secondary actives:

TABLE 3

| Triphasic Tablet Formulations | | | |
|---|---|---|---|
| | Formulation 3 | Formulation 4 | Formulation 5 |
| Norgestimate | 0.180 mg | 0.215 mg | 0.250 mg |
| Ethinyl Estradiol | 0.025 mg | 0.025 mg | 0.025 mg |

The blister pack containing the 7 individual doses of methylcobalamin and the 21 doses of other active can be provided with instructions for the user to complete the 21 days of other (secondary) active steroid hormone contraceptive dosing regimen, in consecutive order starting with the provided doses of Formulation 3, followed by provided doses of Formulation 4, followed by the provided doses of Formulation 5, and finally followed by the doses comprising methylcobalamin (e.g., of either Formulation 1 or Formulation 2).

Doses of Formulations 1 or 2 tablets can be taken by a user during a period of time wherein the user is expecting to experience breakthrough bleeding.

An example of a schedule for a cyclic vitamin B12 compound supplementation regimen practiced in connection with a triphasic birth control regimen is provided as Table 4. Therein, 7 days of hormone phase 1, followed by 7 days of hormone phase 2, following by 7 days of hormone phase 3, followed by 7 days of vitamin B12 compound administration. Such a regimen can be provided as a labeled blister pack, each blister comprising an individual, daily dose unit of appropriate hormone or vitamin B12 compound composition.

TABLE 4

Exemplary vitamin B12 compound administration in connection with a triphasic birth control regimen.

| Days | Administration |
| --- | --- |
| 1-7 | Hormone Phase 1 |
| 8-14 | Hormone Phase 2 |
| 15-21 | Hormone Phase 3 |
| 22-28 | Vitamin B12 Compound |

Cycle repeated after day 28

Additional Exemplary Aspects of the Invention

The following is a non-limiting list of exemplary aspects of the invention, which is intended to further highlight and illuminate various embodiments of the invention in a convenient summary form. Such aspects of the invention include:

1. A method of supplementing vitamin B12 levels in a female experiencing or likely to experience a recurring vaginal discharge of blood comprising orally administering to the female a pharmaceutically acceptable dosage form comprising a methylcobalamin compound for a period of only 3-10 treatment days which are expected to correlate with the period in which vaginal discharge of blood is expected to occur in the female, wherein the method comprises repeating the treatment and non-treatment periods for two or more cycles and the method comprises not administering any methylcobalamin compound dosage form to the woman on any days of the cycle other than the treatment days, and wherein the total amount of methylcobalamin compound administered to the woman by administration of the dosage form in any single cycle does not exceed 35 mcg;
2. The method of aspect 1, wherein the woman has been diagnosed as belonging to a group that is at risk for suffering from a condition associated with vitamin B-12 deficiency;
3. The method of any one of aspects 1-2 wherein the dosage form is free of iron, folic acid, or both;
4. The method of any one of aspects 1-2, wherein the dosage form comprises iron, folic acid, or both;
5. The method of any one of aspects 1-2, wherein the dosage form is free of folic acid and iron, but the woman is using folic acid nutritional supplementation, iron nutritional supplementation, or both;
6. The method of any one of aspects 1-5, wherein the total amount of methylcobalamin compound the woman receives in the course of any cycle is less than about 20 mcg;
7. The method of aspect 6, wherein the amount of methylcobalamin compound supplementation the woman receives on any day of the cycle is less than about 3 mcg;
8. The method of aspect 7, wherein the amount of methylcobalamin compound the woman receives on any day of the cycle is less than 2.5 mcg;
9. The method of any one of aspects 1-8, wherein the dosage form is gluten free, sugar free, or both gluten free and sugar free;
10. The method of any one of aspects 1-9, wherein the woman is receiving treatment with a steroid pharmaceutical agent before, during, and/or after the treatment days;
11. The method of aspect 10, wherein the second oral dosage form comprises one or more conception-regulating pharmaceutically active ingredients;
12. The method of aspect 11, wherein at least one of the conception-regulating pharmaceutically acceptable ingredients comprises an estrogen receptor modulating compound (e.g., an estrogen compound) (or means for modulating an estrogen receptor);
13. The method of aspect 12, wherein the conception-regulating pharmaceutically active ingredients comprise a triphasic steroid birth control treatment;
14. The method of aspect 13, wherein the triphasic conceptive comprises a first phase of a progestogen and an estrogen; a second phase of a progestogen and an estrogen wherein the amount of progestogen is higher than that of the first phase; and a third phase of a progestogen and an estrogen wherein the amount of progestogen is higher than that of the first or the second phase, and wherein the amount of estrogen remains constant throughout all three phases;
15. The method of any one of aspects 1-14, wherein the methylcobalamin compound is added to the dosage form as part of an intermediate methylcobalamin composition comprising about 0.75-1.5% of the methylcobalamin compound;
16. The method of aspect 15, wherein the methylcobalamin compound is a salt of a naturally occurring form of methylcobalamin;
17. The method of any one of aspects 1-16, wherein the dosage form is a tablet;
18. The method of aspect 17, wherein the amount of methylcobalamin compound in each tablet administered to the woman is about 0.002-0.003 wt. % of the tablet;
19. The method of aspect 18, wherein the weight of the tablet is about 50-150 mg;
20. The method of aspect 17 or aspect 18, wherein the tablet comprises about 0.25-0.75 wt. % magnesium stearate;
21. The method of any one of aspects 1-20, wherein the total dose of methylcobalamin compound the woman receives in any cycle is less than about 17.5 mcg;
22. The method of any one of aspects 1-21, wherein the target recipient population has an average age of 40 years or older and wherein the recipient experiences either a consistent or inconsistent menstrual cycle including a period of blood loss or experiences consistent or inconsistent breakthrough bleeding while on a birth control method;
23. A method of detectably or significantly promoting the maintenance or restoration of blood cell levels in a female having a condition associated with a temporary reduction in red blood cells (e.g., a woman undergoing a recurring vaginal discharge of blood) comprising orally administering to a female human subject (e.g., a female subject of between about 15 and about 55 years of age) experiencing a recurring vaginal discharge of blood a pharmaceutically acceptable dosage form comprising a vitamin B12 compound for a period of only 3-10 treatment days (e.g., 3-10 days during the woman's expected bleeding episode, wherein the 3-10 treatment days are expected to correlate with the period of the cycle in which menstruation occurs), wherein the method comprises administering a means for controlling ovulation on days other than the vitamin B12 compound treatment days, wherein together the vitamin B12 treatment period and the ovulation control treatment period define one cycle, and wherein the total amount of vitamin B12 compound administered to the woman by administration of the vitamin B12 dosage form in any single vitamin B12-ovulation control cycle does not exceed 25 mcg;

24. The method of aspect 23, wherein the vitamin B12 compound is a methylcobalamin compound and further wherein the total amount of methylcobalamin compound administered to a woman by administration of the pharmaceutically acceptable dosage form during the vitamin B12 treatment period does not exceed 20 mcg;

25. A method of promoting healthy hematopoiesis in a woman experiencing a recurring vaginal discharge of blood (e.g., breakthrough bleeding or menstruation) comprising orally administering to a female human subject (e.g. a female subject of between about 15 and about 55 years of age) experiencing a recurring vaginal discharge of blood a pharmaceutically acceptable tablet comprising a methylcobalamin compound and a means for disintegrating the tablet upon ingestion for a consecutive daily treatment period comprising no more than 30% of any single month period and wherein the total amount of methylcobalamin compound administered to the woman by administration of the dosage form in any single treatment period does not exceed 25 mcg;

26. A method of detectably or significantly promoting the maintenance or restoration of red blood cell levels in a female having a condition associated with a temporary reduction in red blood cells (e.g., a woman undergoing a recurring vaginal discharge of blood) comprising orally administering to a female human subject (e.g., a female subject of between about 15 and about 55 years of age) experiencing a recurring vaginal discharge of blood a pharmaceutically acceptable dosage form stable at room temperature for at least 24 months comprising a methylcobalamin compound and a means for stabilization of the dosage form for a period of only 3-10 treatment days during the woman's menstruation cycle, wherein the 3-10 treatment days are expected to correlate with the period of the cycle in which vaginal bleeding is expected to occur, wherein the method comprises administering one or more other dosage forms on days other than the methylcobalamin treatment days, and wherein the total amount of methylcobalamin compound administered to the woman by administration of the dosage form in any cycle does not exceed 25 mcg.

The invention claimed is:

1. A method of supplementing vitamin B12 levels in a human female experiencing or expected to experience a temporary reduction in blood cell levels comprising orally administering to the female a pharmaceutically acceptable dosage form comprising a methylcobalamin compound for a treatment period of only 3-10 treatment days which are expected to correlate with a period in which reduced blood cell levels are expected to occur in the female, followed by a non-treatment period to complete one cycle, and repeating the treatment and non-treatment periods for two or more cycles, and wherein the total amount of methylcobalamin compound administered to the female in any single cycle consists of 35 micrograms (mcg) or less.

2. The method of claim 1, wherein the pharmaceutically acceptable dosage form is an oral dosage form and the amount of methylcobalamin compound supplementation the female receives on any day of the cycle is less than about 3 mcg.

3. The method of claim 2, wherein the amount of methylcobalamin compound the female receives on any day of the cycle is less than about 2.5 mcg.

4. The method of claim 3, wherein the total amount of methylcobalamin compound the female receives in the course of any cycle is less than about 20 mcg.

5. The method of claim 4, wherein the total amount of methylcobalamin compound the female receives in the course of any cycle is less than about 17.5 mcg.

6. The method of claim 2, wherein the methylcobalamin compound is added to the dosage form as part of an intermediate methylcobalamin composition comprising about 0.75-1.5 wt. % of the methylcobalamin compound.

7. The method of claim 6, wherein the methylcobalamin compound is a salt of a naturally occurring form of methylcobalamin.

8. The method of claim 2, wherein the dosage form is a tablet having a weight of between about 50 and about 150 mg, and wherein the amount of methylcobalamin compound in each tablet administered to the female is about 0.002-about 0.003 wt. % of the tablet.

9. The method of claim 8, wherein the tablet further comprises about 0.25-about 0.75 wt. % magnesium stearate.

10. The method of claim 8, wherein the method detectably or significantly promotes the maintenance or restoration of blood cell levels in the female experiencing temporary reductions in blood cell levels during recurring periods of vaginal discharge of blood.

11. The method of claim 10, wherein the female is between the ages of 15-55 years.

12. The method of claim 11, wherein the female is 40 years of age or older and (a) has been diagnosed as belonging to a group that is at risk for suffering from a condition associated with vitamin B12 deficiency; (b) experiences either a consistent or inconsistent menstrual cycle including a period of blood loss or experiences consistent or inconsistent breakthrough bleeding while on a birth control method; or (c) has been diagnosed as belonging to a group that is at risk for suffering from a condition associated with vitamin B12 deficiency and experiences either a consistent or inconsistent menstrual cycle including a period of blood loss or experiences consistent or inconsistent breakthrough bleeding while on a birth control method.

13. The method of claim 12, wherein the female is further receiving treatment with a steroid pharmaceutical agent before, during, or after the treatment period, or a combination of two or all thereof.

14. The method of claim 13, wherein the steroid pharmaceutical agent is delivered as a second oral dosage form comprising one or more conception-regulating pharmaceutically active ingredients.

15. The method of claim 14, wherein at least one of the conception-regulating pharmaceutically acceptable ingredients comprises an estrogen receptor modulating compound.

16. The method of claim 15, wherein the conception-regulating pharmaceutically active ingredients comprise a triphasic steroid birth control treatment.

17. The method of claim 16, wherein the triphasic conceptive comprises a first phase of a progestogen and an estrogen; a second phase of a progestogen and an estrogen wherein the amount of progestogen is higher than that of the first phase; and a third phase of a progestogen and an estrogen wherein the amount of progestogen is higher than that of the first or the second phase, and wherein the amount of estrogen remains constant throughout all three phases.

18. The method of claim 17 wherein the methylcobalamin dosage form is free of iron, free of folic acid free of gluten, free of sugar, or any two or more thereof.

19. The method of claim 17, wherein the methylcobalamin dosage form comprises iron, folic acid, or both.

20. The method of claim 18, wherein the methylcobalamin dosage form is free of folic acid and iron, but the female is using folic acid nutritional supplementation, iron nutritional supplementation, or both during the cycle in which the methylcobalamin dosage form is administered.

\* \* \* \* \*